US012564345B2

(12) United States Patent
Ishikawa et al.

(10) Patent No.: US 12,564,345 B2
(45) Date of Patent: Mar. 3, 2026

(54) MEDICAL APPARATUS, AND IMAGE GENERATION METHOD FOR VISUALIZING TEMPORAL TRENDS OF BIOMAGNETIC DATA ON AN ORGAN MODEL

(71) Applicant: Asahi Intecc Co., Ltd., Seto (JP)

(72) Inventors: Masatomo Ishikawa, Seto (JP); Takayuki Hori, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 392 days.

(21) Appl. No.: 18/136,889

(22) Filed: Apr. 20, 2023

(65) Prior Publication Data

US 2023/0255535 A1     Aug. 17, 2023

Related U.S. Application Data

(63) Continuation of application No. PCT/JP2020/040073, filed on Oct. 26, 2020.

(51) Int. Cl.
*A61B 5/242*       (2021.01)
*A61B 5/00*        (2006.01)

(52) U.S. Cl.
CPC ............ *A61B 5/242* (2021.01); *A61B 5/0044* (2013.01); *A61B 5/743* (2013.01)

(58) Field of Classification Search
CPC ........ A61B 5/242; A61B 5/0044; A61B 5/743
USPC ......................................................... 345/619
See application file for complete search history.

(56) References Cited

U.S. PATENT DOCUMENTS 6,522,908 B1   2/2003   Miyashita et al.
9,204,927 B2 *   12/2015   Afonso .............. A61B 18/1492

2001/0009974 A1   7/2001   Reisfeld
2004/0039291 A1 *   2/2004   Nakai .................. A61B 6/5247
                                         600/508
2005/0148844 A1   7/2005   Ogata et al.
2009/0022378 A1   1/2009   Nemoto

FOREIGN PATENT DOCUMENTS

CN     107708540 A     2/2018
EP       0470270 A1 *   2/1992   ............. A61B 5/245
JP     2001-170018 A    6/2001
JP      4027867 B2     12/2007

(Continued)

OTHER PUBLICATIONS

International Search Report and Written Opinion mailed on Dec. 22, 2020, received for PCT Application PCT/JP2020/040073, filed on Oct. 26, 2020, 9 pages including English Translation.

(Continued)

*Primary Examiner* — David T Welch
*Assistant Examiner* — Ryan Allen Barham
(74) *Attorney, Agent, or Firm* — XSENSUS LLP

(57) ABSTRACT

A system provides for the visualization of an organ's electrical activity. Circuitry acquires image information to generate an anatomical organ model and also acquires biomagnetic field information from the organ. An electrocardiogramrent image is generated from the biomagnetic field information. This current image expresses over-time changes in the organ's electrical current by using a change in a color attribute to visually represent the temporal trend of the current rising or falling at various positions. A final composite image is generated by superposing the current image onto the anatomical organ model.

18 Claims, 16 Drawing Sheets

(56) References Cited

FOREIGN PATENT DOCUMENTS

| | | | |
|---|---|---|---|
| JP | 4597329 | B2 | 12/2010 |
| WO | 02/05714 | A1 | 1/2002 |
| WO | 2006109692 | A1 | 10/2006 |
| WO | 2016/205731 | A1 | 12/2016 |

OTHER PUBLICATIONS

English-language translation of Japanese Office Action issued Jun. 24, 2025, in corresponding Japanese Patent Application No. 2022-558608, 13pp.
University of Tsukuba, Hitachi, Ltd., Identifying the site of arrhythmias with high accuracy—using synthetic technology of magnetocardiograms and cardiac CT images—, Tsukuba Journal press release, Aug. 1, 2019, https://www.tsukuba.ac.jp/journal/images/pdf/190725ieda-1.pdf (the English-language translation of Japanese Office Action serves as a statement of relevance).

* cited by examiner

MI1(t1)
MI2(t1)
MI3(t1)
MI4(t1)
MI5(t1)

DM(t1)

DM

DM(t1)          DM(tn)

...

MEDICAL APPARATUS, AND IMAGE GENERATION METHOD FOR VISUALIZING TEMPORAL TRENDS OF BIOMAGNETIC DATA ON AN ORGAN MODEL

CROSS-REFERENCE TO RELATED APPLICATION

This application is a continuation application of International Application No. PCT/JP2020/040073 filed Oct. 26, 2020, the entire contents of which is incorporated herein by reference.

TECHNICAL FIELD

The disclosed embodiments relate to a medical apparatus, and an image generation method.

BACKGROUND

There are known techniques for visualizing a condition of an organ in a living body. For example, Patent Literatures 1 and 2 disclose a technique in which a current vector flowing through a heart is estimated from results of heart measurements, and, in a heart model, the current vector is indicated by arrows and colors (color mapping display).

CITATION LIST

Patent Literature

Patent Literature 1: Japanese Patent No. 4597329
Patent Literature 2: Japanese Patent No. 4027867

SUMMARY

Technical Problems

For example, for treatment of arrhythmia or the like, there is a demand to improve a technique of providing treatment while visually checking a condition of a heart including a lesion (arrhythmia site in a case of arrhythmia treatment). However, the techniques described in Patent Literatures 1 and 2 had a concern that the arrows indicating the current vectors obstructed a surgeon's view and hindered the surgeon from checking the heart condition. As described above, even the above-described prior arts still had room for improvements in the technique of displaying a condition of a heart including a lesion. Such problems are not limited to the heart but are common to treatments or diagnoses of all organs through which a bioelectric current flows, such as brain and kidney.

The disclosed embodiments have been made to solve the above-described problems, and the disclosed embodiments are directed to improving the technique of displaying a condition of an organ including a lesion.

Solutions to Problems

The disclosed embodiments have been made to solve at least some of the problems described above and other problems, and can be implemented as the following aspects.

(1) According to an aspect of the disclosed embodiments, a medical apparatus is provided. The medical apparatus includes: an image information acquisition portion that acquires image information including a magnetic resonance imaging (MRI) image or a computerized tomography (CT)

image of an organ in a living body; a biomagnetic field information acquisition portion that acquires biomagnetic field information from a biomagnetic field generated by the organ; a model image generation portion that generates, from the image information, an organ model image of the organ two-dimensionally or three-dimensionally expressed; an electrocardiographic current image generation portion that generates an electrocardiographic current image in which an over-time change in a current flowing through each position of the organ, acquired from the biomagnetic field information, is expressed by a change in a color attribute; and a composite image generation portion that generates a composite image in which the organ model image and the electrocardiographic current image are superposed.

According to this configuration, the medical apparatus generates a composite image in which the organ model image of the organ two-dimensionally or three-dimensionally expressed, and the electrocardiographic current image presenting the over-time change in the current flowing through each position of the organ are superposed. Thereby, the surgeon can intuitively recognize the change in the current flowing through each position of the organ using the composite image. In the electrocardiographic current image in the composite image, the over-time change in the current flowing through each position of the organ is expressed by the change in the color attribute. Thus, compared to the conventional arrow indication for current vectors, the medical apparatus according to the disclosed embodiments has no concern that arrows indicating current vectors obstruct a surgeon's view and hinder the surgeon from checking a condition of an organ. As a result, a time required for detecting a lesion (e.g., arrhythmia site) can be shortened, and efficiency and safety of a procedure can be improved.

(2) The medical apparatus according to the above aspect may be configured such that the electrocardiographic current image generation portion expresses the change in the color attribute by changing any of hue, chroma, brightness, and a combination thereof.

According to this configuration, the electrocardiographic current image generation portion generates an electrocardiographic current image in which the change in the color attribute is expressed by changing any of hue, chroma, brightness, and a combination thereof. Thereby, the surgeon can more intuitively recognize the change in the current flowing through each position of the organ.

(3) The medical apparatus according to the above aspects may be configured such that the electrocardiographic current image generation portion generates the electrocardiographic current image in which at least one of hue, chroma, and brightness on a part corresponding to a part through which a relatively high current flows among the positions of the organ at a predetermined time is made higher than those of the other parts at the same time.

According to this configuration, the electrocardiographic current image generation portion generates an electrocardiographic current image in which at least one of hue, chroma, and brightness on a part corresponding to the part through which a relatively high current flows is made higher than the other parts. Thereby, the surgeon can more intuitively recognize the change in the current flowing through each position of the organ.

(4) The medical apparatus according to the above aspects may be configured such that, at a certain position of the organ, when a current value rises over time, the electrocardiographic current image generation portion generates the electrocardiographic current image with the color attribute changed in a first pattern, and when the current value drops over time, the electrocardiographic current image generation portion generates the electrocardiographic current image with the color attribute changed in a second pattern different from the first pattern.

According to this configuration, the electrocardiographic current image generation portion generates an electrocardiographic current image in which, when the current value rises over time at a certain position of the organ, the color attribute is changed in a first pattern, and when the current value drops over time, the color attribute is changed in a second pattern. Thereby, the pattern of change in the color attribute allows the surgeon to intuitively recognize whether a current value at a certain position of the organ is rising or dropping.

(5) The medical apparatus according to the above aspects may be configured such that the biomagnetic field information include information on a magnetic field intensity distribution of the biomagnetic field generated by the organ, the medical apparatus further includes a magnetic field intensity distribution image generation portion that generates, from the biomagnetic field information, a magnetic field intensity distribution image presenting an intensity of the biomagnetic field at each position of the organ, and the composite image generation portion generates a composite image in which the magnetic field intensity distribution image is further superposed on the organ model image and the electrocardiographic current image.

According to this configuration, the composite image generation portion generates a composite image in which the magnetic field intensity distribution image is further superposed on the organ model image and the electrocardiographic current image. Thereby, the surgeon can recognize the intensity of the biomagnetic field at each position of the organ from the magnetic field intensity distribution image in the composite image, and the efficiency and safety of the procedure can be further improved.

(6) According to an aspect of the disclosed embodiments, an image generation method is provided. This image generation method includes: a step of acquiring image information including an MRI image or a CT image of an organ in a living body; a step of acquiring biomagnetic field information from a biomagnetic field generated by the organ; a step of generating, from the image information, an organ model image of the organ two-dimensionally or three-dimensionally expressed; a step of generating an electrocardiographic current image in which an over-time change in a current flowing through each position of the organ, acquired from the biomagnetic field information, is expressed by a change in a color attribute; and a step of generating a composite image in which the organ model image and the electrocardiographic current image are superposed.

The disclosed embodiments can be achieved in various modes, and can be achieved in modes such as medical apparatuses (image generation apparatus) that generate images for display, image generation methods, medical systems including medical apparatuses, production methods of these apparatuses and systems, and computer programs that achieve functions of these apparatuses and systems.

DETAILED DESCRIPTION

First Embodiment

Figure 1:
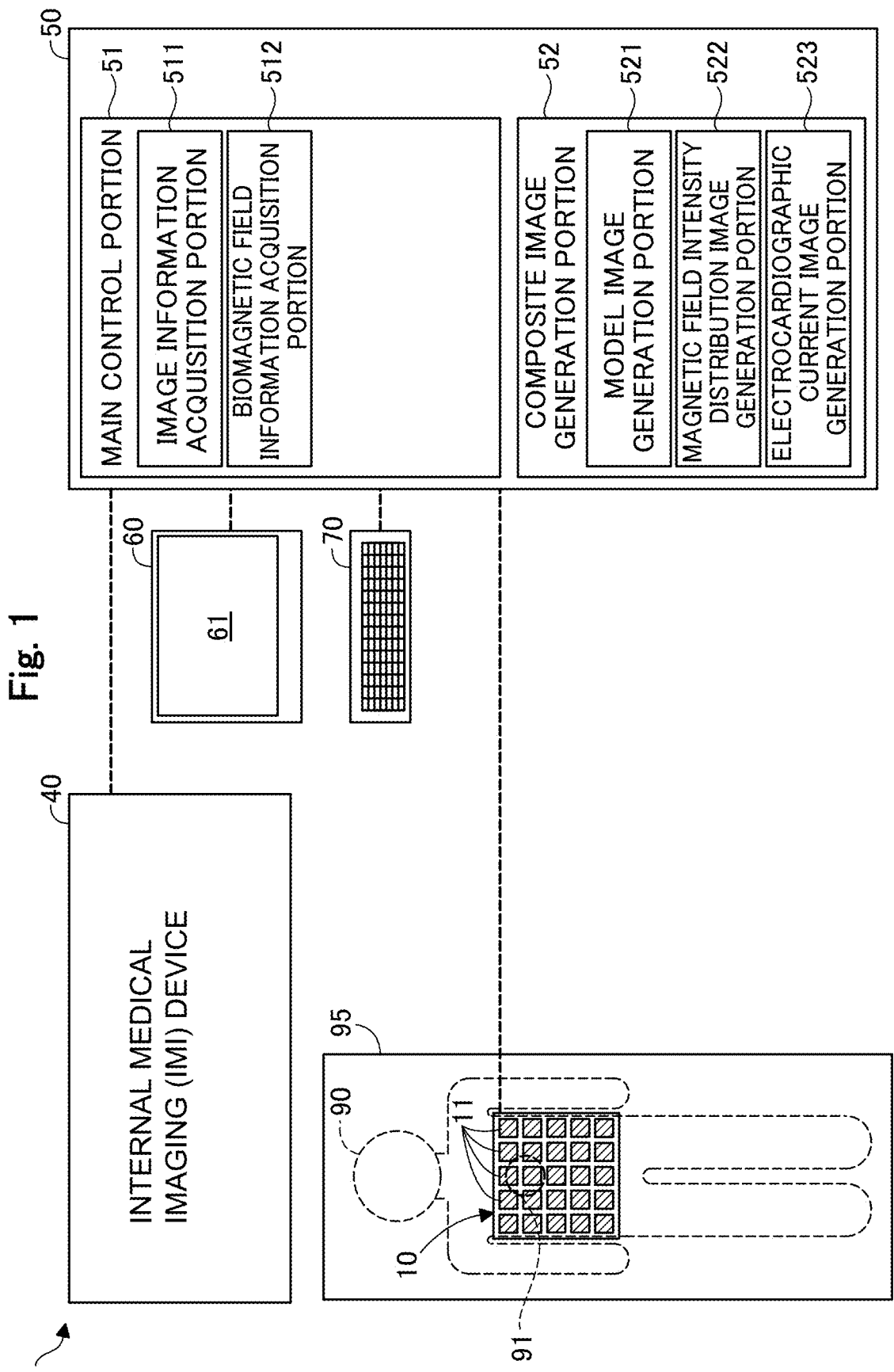
FIG. 1 is an explanatory diagram illustrating a configuration of a medical apparatus.

FIG. 1 is an explanatory diagram illustrating a configuration of a medical apparatus 1. The medical apparatus 1 is used for treatment or diagnosis of a living body (herein, a human body) 90, and can generate and display an electrocardiographic current image in which an over-time change in a current flowing through each position of an organ of the human body 90 is expressed by a change in a color attribute. The medical apparatus 1 includes a magnetic sensor array 10, an internal medical imaging device 40, a computer 50, a monitor 60, and an operating portion 70. The medical apparatus 1 used for treating arrhythmia will be explained in the following examples.

The magnetic sensor array 10 is a device for detecting information on a biomagnetic field generated by the human body 90 to be treated or diagnosed (hereinafter also referred to as "biomagnetic field information"). The biomagnetic field information include a biomagnetic field intensity and a biomagnetic field direction. A plurality of magnetic sensors 11 are arranged on the magnetic sensor array 10. The plurality of magnetic sensors 11 are longitudinally and laterally arranged side-by-side in a matrix. The magnetic sensors 11 are a device that detects biomagnetic field information, and examples thereof may include a GHz-Spin-Rotation Sensor (GSR) sensor, a magnetoresistive effect device (MR), a magnetic impedance device (MI), and a superconducting quantum interference device (SUQUID).

The magnetic sensor array 10 is located around a center of a bed 95 on which the human body 90 lies. The magnetic sensor array 10 may be configured to be attached to the human body 90 during treatment or diagnosis. Furthermore, the magnetic sensor array 10 may be configured to be attached to the human body 90 during treatment. For example, the magnetic sensor array 10 may be configured to have a band shape to be wrapped around the human body 90 or may be configured to have a garment or cap shape. In these cases, the magnetic sensors 11 may be arranged along the shape of the human body 90. The magnetic sensor array 10 may be composed of two or more plates which are three-dimensionally arranged on one or both of the front and back of the human body, and one or both of the sides of the human body. An example of detecting cardiac magnetic field information (intensity, direction, etc. of a cardiac magnetic field) generated by a heart 91 as one of organs of the human body 90 using the magnetic sensor array 10 will be explained below.

The internal medical imaging device 40 may include a computerized tomography (CT) imaging device. The CT device may include, inside a gantry (mount), a tube bulb that emits X-rays and an arc-shaped detector that detects X-rays to generate a CT image presenting a shape of the heart 91 when the tube bulb rotates by 360° around the human body 90 lying on the bed 95, and output image information including the CT image to the computer 50. The internal medical imaging device 40 may be a magnetic resonance imaging (MRI) image device instead of the CT device, as an apparatus that generates images presenting the shape of the organ inside the human body 90. That is, the medical apparatus 1 may acquire the image information including an MRI image instead of the image information including the CT image.

The computer 50 controls the overall medical apparatus 1 and is electrically connected to each of the magnetic sensor array 10, the internal medical imaging device 40, the monitor 60, and the operating portion 70. The computer 50 includes a central processing unit (CPU), a read-only memory (ROM), and a random access memory (RAM), where a computer program stored in the ROM or other non-transitory computer readable storage device is developed to the RAM, the computer program is executed by the CPU to execute functions of a main control portion 51 and a composite image generation portion 52. As used herein 'computer' refers to circuitry that may be configured via the execution of computer readable instructions, and the circuitry may include one or more local processors (e.g., CPU's), and/or one or more remote processors, such as a cloud computing resource, or any combination thereof.

The main control portion 51 transmits and receives information to/from the magnetic sensor array 10, the internal medical imaging device 40, the monitor 60, and the operating portion 70 to control the entire medical apparatus 1. The main control portion 51 includes an image information acquisition portion 511 and a biomagnetic field information acquisition portion 512. The image information acquisition portion 511 acquires the information (hereinafter also referred to as "image information"), e.g., a CT image or an MRI of the human body 90 through control of the internal medical imaging device 40. The biomagnetic field information acquisition portion 512 acquires information on the biomagnetic field generated by the human body 90 (biomagnetic field information) through control of the magnetic sensor array 10. That is, the main control portion 51 functionally serves as a so-called console for the internal medical imaging device 40 and the magnetic sensor array 10. The image information acquisition portion 511 and the biomagnetic field information acquisition portion 512 will be described below in detail.

The composite image generation portion 52 generates an organ model image, an electrocardiographic current image, and a composite image with the combined these images, and displays the generated composite image on the monitor 60. The composite image generation portion 52 includes a model image generation portion 521, a magnetic field intensity distribution image generation portion 522, and an electrocardiographic current image generation portion 523. Each of these functional portions will be described below in detail.

The monitor 60 is a display portion including a display screen 61 and is composed of a liquid crystal display and the like. The medical apparatus 1 may include a display portion other than the monitor 60. For example, the medical apparatus 1 may include smart glasses including a display screen, or a projector that projects images. The operating portion 70 is composed of any means such as a keyboard, operation buttons, a touch panel, a foot switch, and a voice recognition device. The operating portion 70 is operated by the surgeon to switch contents displayed on the display screen 61.

Figure 2:
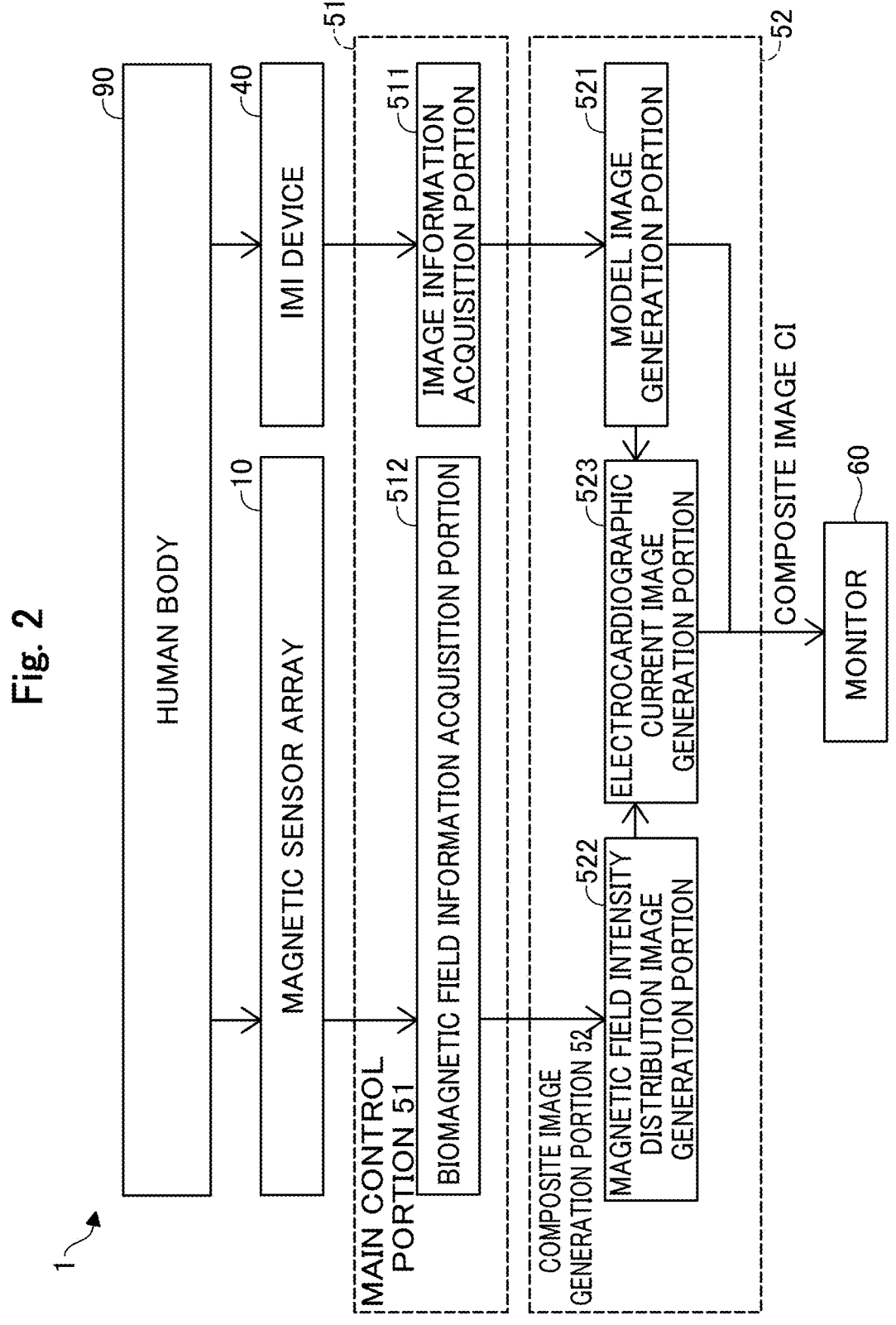
FIG. 2 is a functional block diagram illustrating a main control portion and a composite image generation portion.
Figures 3A, 3B:
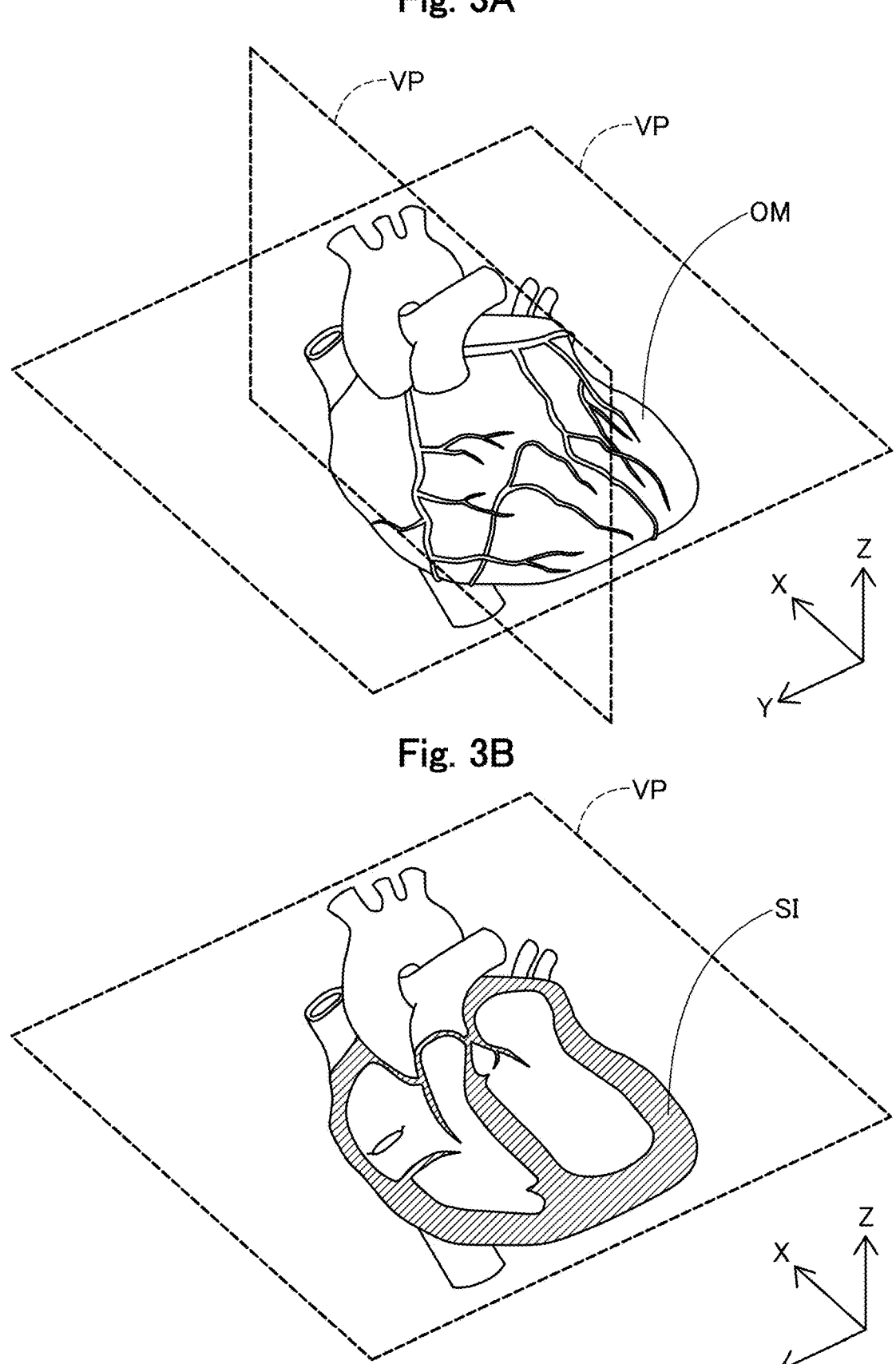
FIGS. 3A and 3B are explanatory diagrams illustrating a three-dimensional organ model and an organ model image.

FIG. 2 is a functional block diagram illustrating the main control portion 51 and the composite image generation portion 52. FIGS. 3A and 3B are explanatory diagrams illustrating a three-dimensional organ model OM and an organ model image SI. FIG. 3A illustrates an example of a three-dimensional organ model OM, and FIG. 3B illustrates an example of an organ model image SI. In the image information acquisition portion 511 of the main control portion 51, the image information image is acquired from internal medical imaging device 40 through control of the internal medical imaging device 40, and the image information are stored in a storage portion of the computer 50. Specifically, in the image information acquisition portion 511, cross-sections of the entire heart 91 are photographed at a time interval to acquire image information including cross-sections of the entire heart 91 at the time interval. Furthermore, in the image information acquisition portion 511, the image information may be directly acquired through control of the internal medical imaging device 40, or otherwise the image information may be acquired from a storage medium storing the previously acquired image information.

The model image generation portion 521 of the main control portion 51 generates the three-dimensional organ model OM illustrated in FIG. 3A from the image information acquired by the image information acquisition portion 511. Various existing techniques are applicable as the specific technique of generating the three-dimensional organ model OM from the image information including the CT image or the MRI by the biomagnetic field information acquisition portion 512. In the example illustrated in the figure, the three-dimensional organ model OM is composed of stereoscopic image data presenting external and internal shapes of the heart 91. In the model image generation portion 521, cross-sectional images (a plurality of successive CT images or an MRI) of the entire heart 91 acquired by the image information acquisition portion 511 at a certain time are integrated to generate the three-dimensional organ model OM of the heart 91 at this time. Then, in the model image generation portion 521, the three-dimensional organ models OM of the heart 91 at different times are integrated to generate the dynamic three-dimensional organ model OM that changes over time.

In the model image generation portion 521 of the composite image generation portion 52, this dynamic three-dimensional organ model OM is captured on a virtual plane VP set at any position to generate an organ model image SI in which the heart 91 is three-dimensionally expressed. The position and direction of the virtual plane VP is set to any position and direction desired by the surgeon by operating the operating portion 70. For example, when the virtual plane VP intersects with the three-dimensional organ model OM, an organ model image SI presenting the cross-section of the three-dimensional organ model OM is generated as illustrated in FIG. 3B. When the set virtual plane VP does not intersect with the three-dimensional organ model OM, an organ model image SI presenting an appearance (outer surface) of the three-dimensional organ model OM viewed from the virtual plane VP is generated.

The model image generation portion 521 may generate an organ model image SI in which the heart 91 is two-dimensionally expressed. The two-dimensional organ model image SI presents only a surface of a part intersecting with the virtual plane VP in the three-dimensional organ model OM. The three-dimensional organ model image SI presents not only the part intersecting with the virtual plane VP but also a part of the three-dimensional organ model OM in a depth direction viewed from the virtual plane VP. The dimension (2D/3D/both) of the image generated by the model image generation portion 521 can be arbitrarily set by the surgeon by operating the operating portion 70.

The three-dimensional organ model OM includes information on a coordinate position of a part corresponding to a specific site of the heart 91. The "information on a coordinate position of a specific site of the heart 91" refer to e.g., information on a position of sinus node, a position of atrioventricular node, a direction of His bundle, a position of Purkinje's fiber, and the like. The information on the coordinate position of the specific site of the heart 91 can be acquired e.g., by fitting between a contour image displaying a general positional relationship of these specific sites (sinus node, atrioventricular node, His bundle, Purkinje's fiber, etc.) and the three-dimensional organ model OM generated by the model image generation portion 521.

Figure 4:
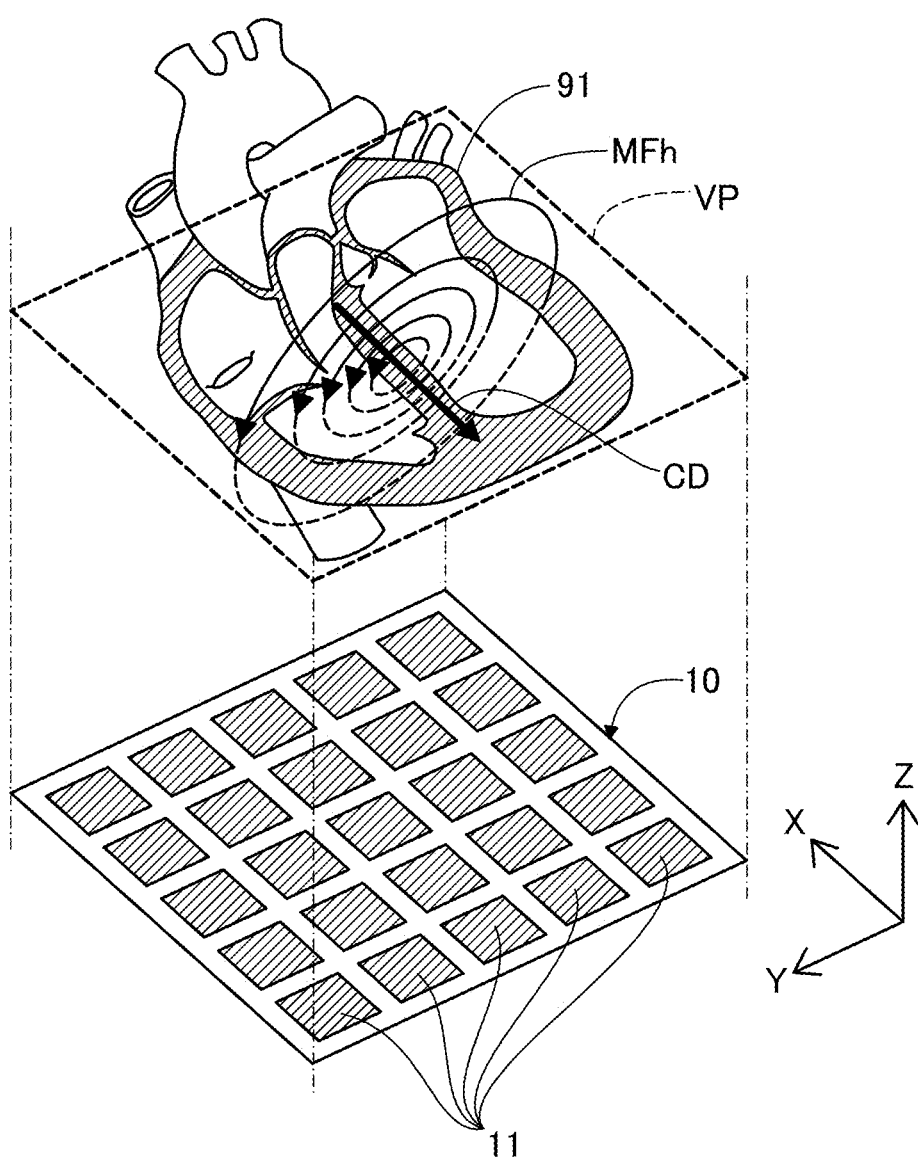
FIG. 4 is a schematic diagram illustrating a method for acquiring biomagnetic field information using a magnetic sensor array.

FIG. 4 is a schematic diagram illustrating a method for acquiring biomagnetic field information using the magnetic sensor array 10. In the biomagnetic field information acquisition portion 512 of the main control portion 51 (FIG. 2), the biomagnetic field information are acquired through control of the magnetic sensor array 10, and the biomagnetic field information are stored in the storage portion of the computer 50. As mentioned above, the biomagnetic field information include an intensity and a direction of a biomagnetic field MFh generated by an organ inside the human body 90. As illustrated in FIG. 4, in the heart 91, electric signals CD are generated from a sinus node to contract atria and ventricles. The magnetic sensor array 10 detects an intensity and a direction of the biomagnetic field MFh, generated by the electric signals CD, and the biomagnetic field information acquisition portion 512 acquires the intensity and direction of the biomagnetic field MFh as biomagnetic field information.

If an organ has a lesion (e.g. arrhythmia of the heart 91), the intensity and direction of the biomagnetic field MFh in the biomagnetic field information are affected by the lesion. In other words, the intensity and direction of the biomagnetic field MFh of the organ with the lesion are different from those of a healthy organ without a lesion. This makes it possible to identify a position of a lesion in an organ from biomagnetic field information (by comparison with a biomagnetic field MFh of a healthy organ). Thus, it can be said that the biomagnetic field information acquired by the biomagnetic field information acquisition portion 512 includes information on the lesion of the organ.

Figure 5A:
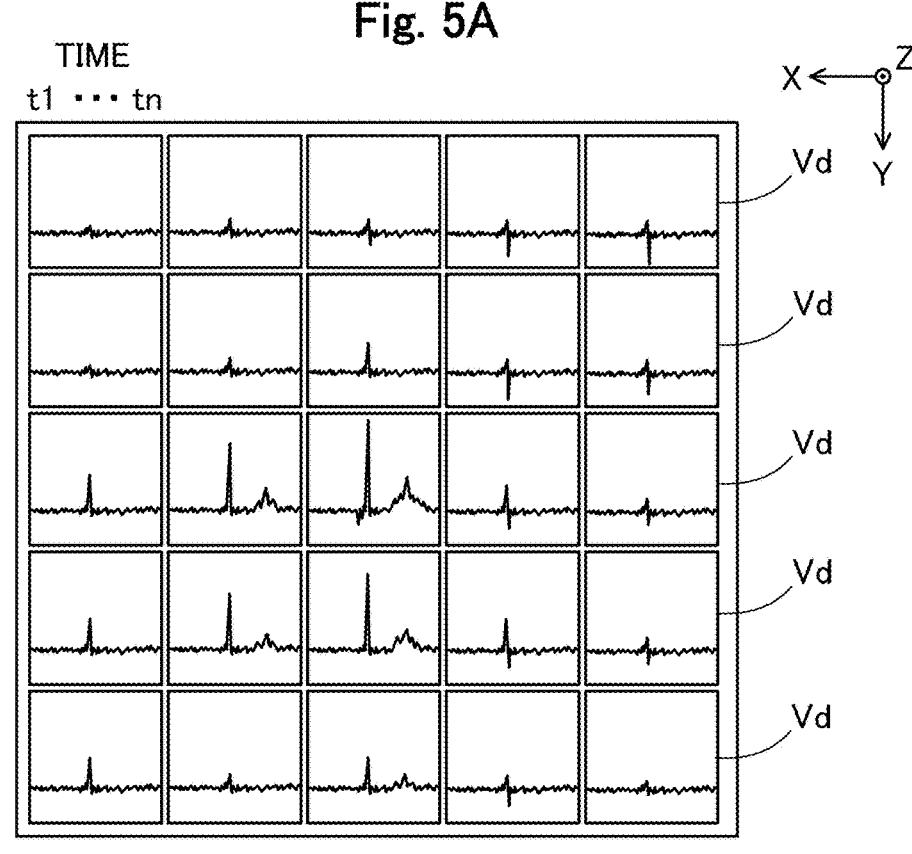
FIGS. 5A and 5B are schematic diagrams illustrating a method for generating a magnetic field intensity distribution image.
Figure 5B:
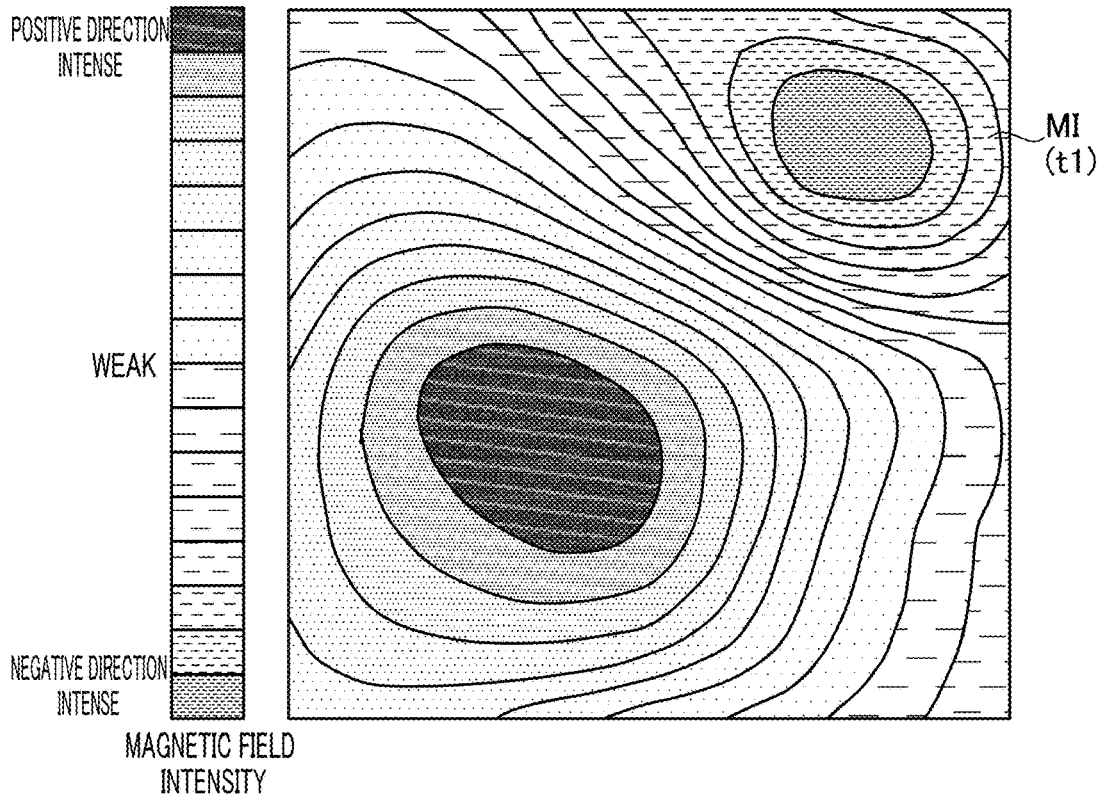

FIGS. 5A and 5B are schematic diagrams illustrating a method for generating a magnetic field intensity distribution image MI. FIG. 5A is a diagram illustrating an example of intensities (detection values Vd) of the biomagnetic field MFh, detected by the respective magnetic sensors 11 of the magnetic sensor array 10. FIG. 5B is a diagram illustrating an example of the magnetic field intensity distribution image MI. In the magnetic sensor array 10, the magnetic sensors 11 are arranged in a matrix on a two-dimensional plane (XY plane). Thereby, the magnetic sensor array 10 can detect an intensity (detection value Vd) of the biomagnetic field MFh at each position on the two-dimensional plane as illustrated in FIG. 5A. FIG. 5A illustrates a time-series change in the intensity of the biomagnetic field MFh at each position on the two-dimensional plane (XY plane). From the temporal change in the intensity of the biomagnetic field MFh at each position on the two-dimensional plane, the magnetic sensor array 10 can detect the direction of the biomagnetic field MFh on the two-dimensional plane. Furthermore, the magnetic sensor 11 is configured to detect a change in the intensity of the biomagnetic field MFh in a normal direction (Z-direction) of the two-dimensional plane. Herein, each of the magnetic sensors 11 includes a plurality of (e.g. two) elements arranged in the normal direction of the two-dimensional plane so as to detect the intensity of the biomagnetic field MFh at a position relatively close to the heart 91 in the normal direction (Z-direction) and the intensity of the biomagnetic field MFh at a position relatively far from that position. This configuration makes it possible for the magnetic sensor array 10 to detect the intensity and direction of the biomagnetic field MFh on an arbitrary virtual plane VP (XY plane) intersecting with the heart 91. The magnetic sensor array 10 outputs, to the biomagnetic field information acquisition portion 512, these biomagnetic field information including these intensities of the biomagnetic field MFh, detected by the respective magnetic sensors 11.

Figure 6:
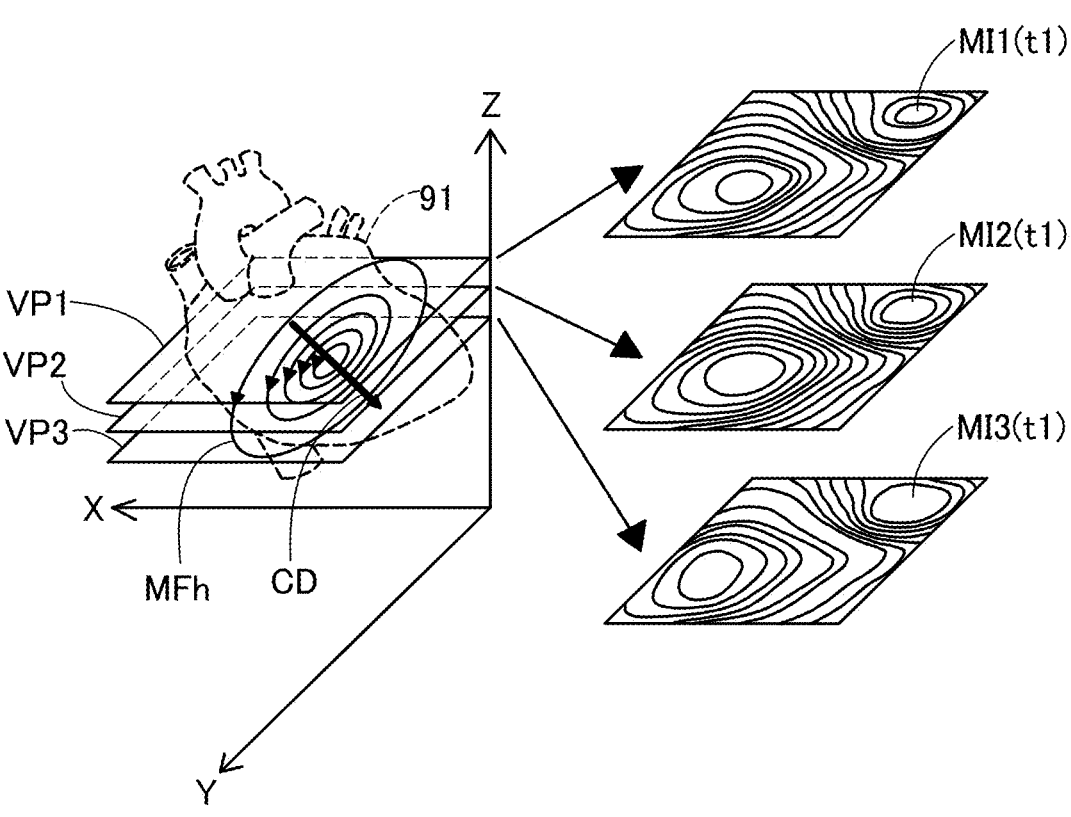
FIG. 6 is an explanatory diagram illustrating magnetic field intensity distribution images on a plurality of virtual planes of a heart.

FIG. 6 is an explanatory diagram illustrating magnetic field intensity distribution images MI1 to MI3 on different virtual planes VP1 to VP3 of the heart 91. The magnetic field intensity distribution image generation portion 522 of the composite image generation portion 52 generates the magnetic field intensity distribution image MI illustrated in FIG. 5B from the biomagnetic field information acquired by the biomagnetic field information acquisition portion 512. FIG. 5B illustrates a magnetic field intensity distribution image MI in which the intensity of the biomagnetic field MFh at each position in the two-dimensional plane (XY plane) is expressed in a form of contour lines, as an example of the magnetic field intensity distribution image MI. The intensity of the biomagnetic field MFh may be expressed in a manner other than contours, such as color gradation. From the biomagnetic field information at a certain time t1, the magnetic field intensity distribution image generation portion 522 can generate the magnetic field intensity distribution image MI on the arbitrary virtual plane VP intersecting with the heart 91. FIG. 6 illustrates, as an example, magnetic field intensity distribution images MI1, MI2, and MI3 corresponding to three virtual planes VP1, VP2, and VP3 respectively at the time t1.

Figures 7A, 7B, 7C:
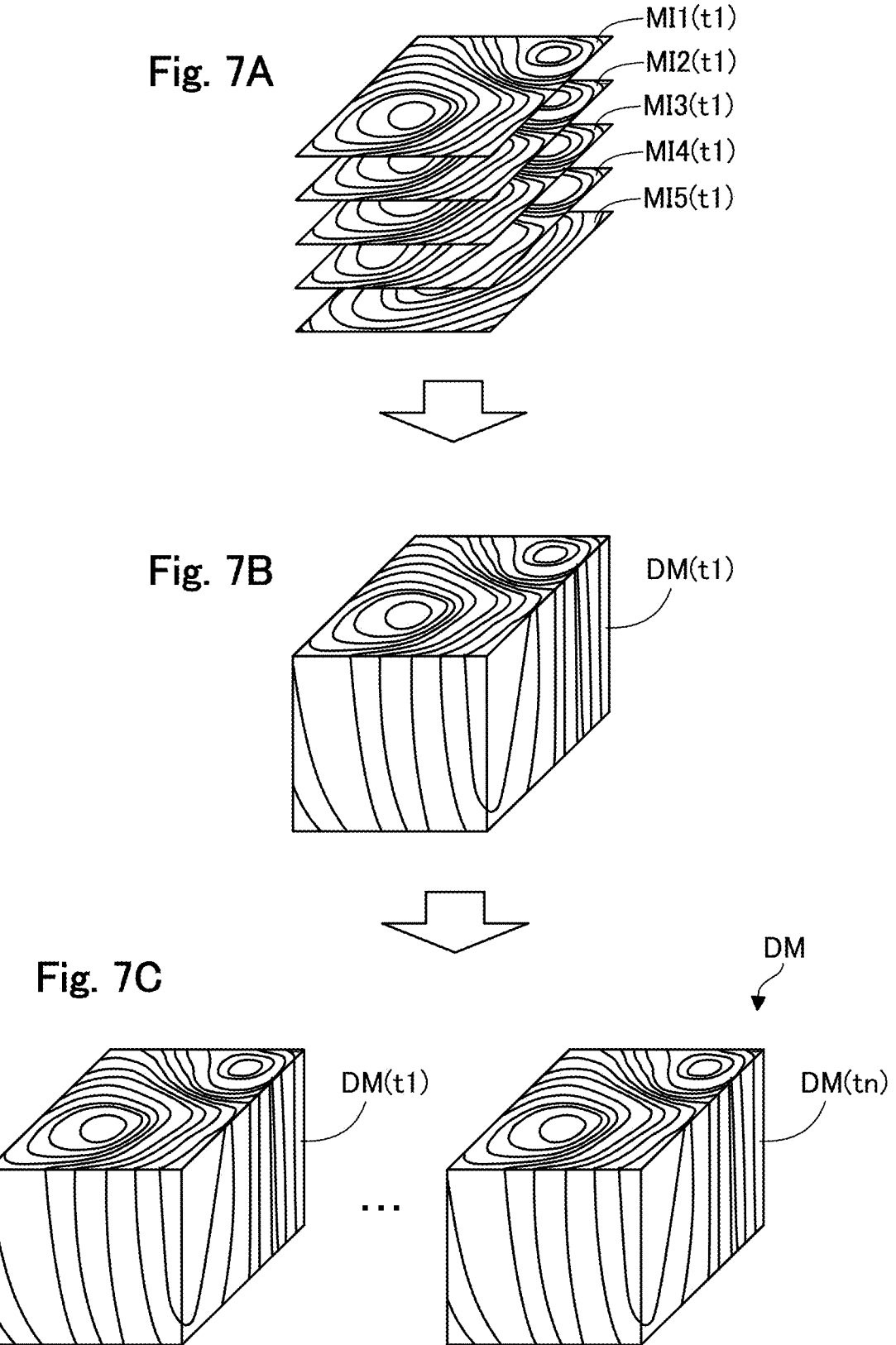
FIGS. 7A to 7C are schematic diagrams illustrating a method for generating a three-dimensional magnetic field intensity distribution model.

FIGS. 7A to 7C are schematic diagrams illustrating a method for generating a three-dimensional magnetic field intensity distribution model DM. FIG. 7A is a diagram illustrating an example of magnetic field intensity distribution images MI1 to MI5 acquired from five different virtual planes. FIG. 7B is a diagram illustrating an example of a three-dimensional magnetic field intensity distribution model DM acquired from the magnetic field intensity distribution images MI1 to MI5. FIG. 7C is a diagram illustrating an example of a dynamic three-dimensional magnetic field intensity distribution model DM that changes over time. Furthermore, in the magnetic field intensity distribution image generation portion 522, the magnetic field intensity distribution images MI1 to MI5 generated as described above (a plurality of successive magnetic field intensity distribution images MI) at a certain time t1 are integrated as illustrated in FIG. 7A to generate the three-dimensional magnetic field intensity distribution model DM at the time t1 as illustrated in FIG. 7B. Subsequently, in the magnetic field intensity distribution image generation portion 522, the three-dimensional magnetic field intensity distribution models DM of the heart 91 at each of different times t1 to tn (n is a natural number) are integrated to generate a dynamic three-dimensional magnetic field intensity distribution model DM that changes over time, as illustrated in FIG. 7C.

The magnetic field intensity distribution image generation portion 522 may generate a two-dimensional magnetic field intensity distribution image MI. The two-dimensional magnetic field intensity distribution image MI presents only the magnetic field intensity distribution of the part intersecting with the virtual plane VP in the three-dimensional magnetic field intensity distribution model DM. The three-dimensional magnetic field intensity distribution image MI presents a magnetic field intensity distribution of the entire three-dimensional magnetic field intensity distribution model DM viewed from the virtual plane VP or a part included in any spatial region in the three-dimensional magnetic field intensity distribution model DM. Therefore, the three-dimensional magnetic field intensity distribution image MI also presents a depth direction of the magnetic field intensity distribution. The dimension (2D/3D/both) of the image generated by the magnetic field intensity distribution image generation portion 522 can be arbitrarily set by the surgeon through the operation of the operating portion 70.

The three-dimensional magnetic field intensity distribution model DM includes not only information on the direction and intensity of the biomagnetic field MFh but also information on a coordinate position of a portion corresponding to a specific site of the heart 91. The "information on a coordinate position of a specific site of the heart 91" can be information on a position of sinus node, a position of atrioventricular node, a direction of His bundle, a position of Purkinje's fiber, and the like, similarly to the three-dimensional organ model OM. Information on a coordinate position of a specific site of the heart 91 can be specified e.g. from a change in the magnetic field generated by the electric signals CD. For example, the sinus node is a part serving as an origin of the electric signals CD and the atrioventricular node is a part serving as a relay point of the electric signals CD, and therefore they can be identified from the generation position of the electric signals CD, the flow direction of the electric signals, and the like.

Figure 8A:
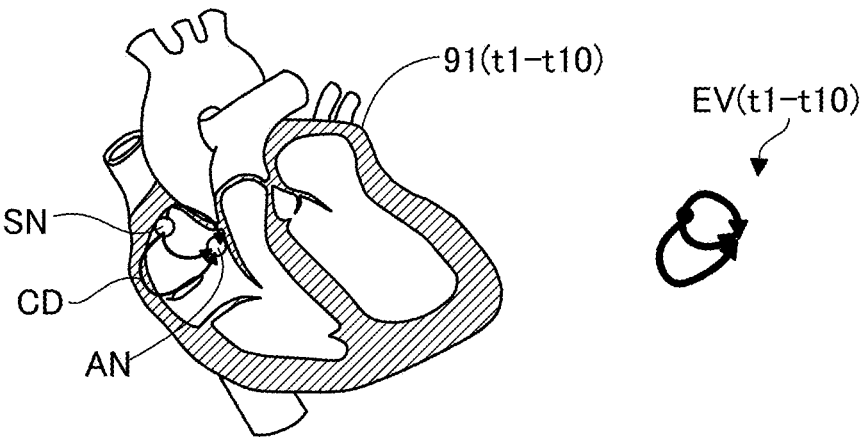
FIGS. 8A to 8C are schematic diagrams illustrating a method for acquiring an over-time change in a current flowing through the heart.
Figure 8B:
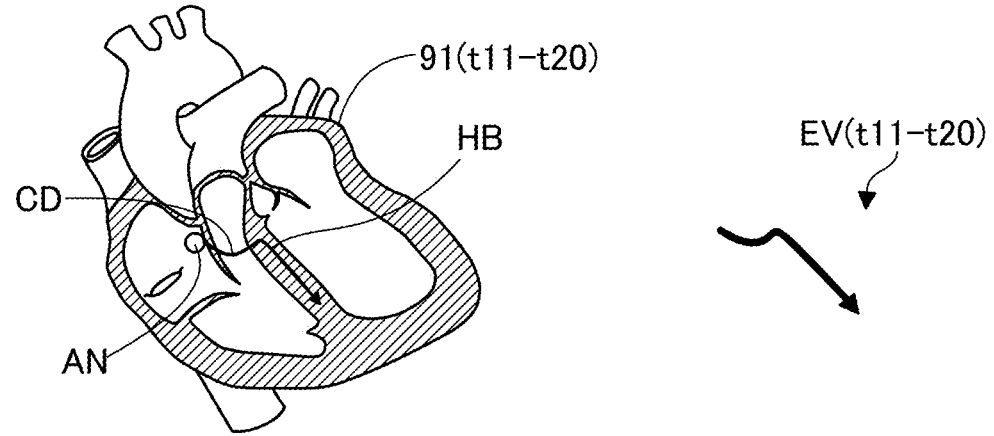
Figure 8C:
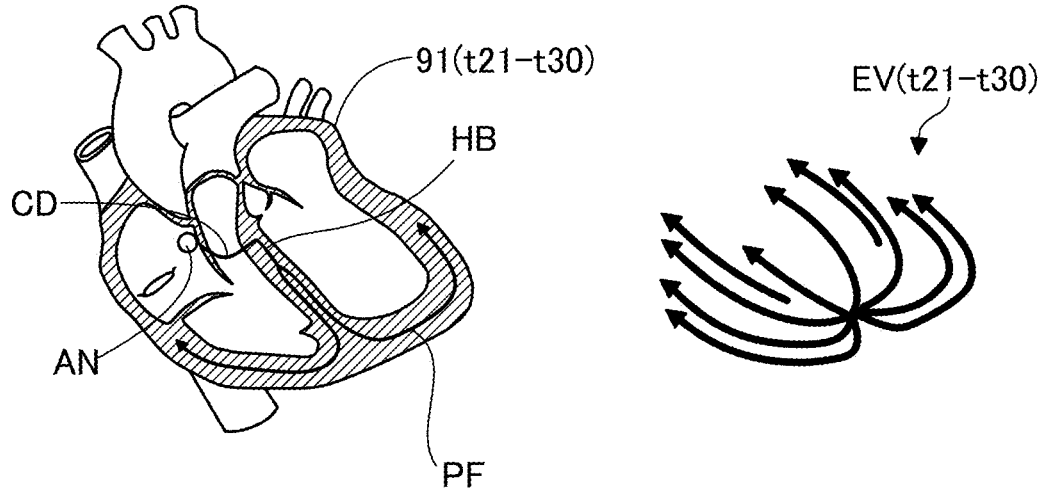

FIGS. 8A to 8C are schematic diagrams illustrating a method for acquiring an over-time change in a current EV flowing through the heart 91. FIG. 8A illustrates an example of electric signals CD that flow through the heart 91 at certain times t1 to t10 and a current EV (t1 to t10) at that time. FIG. 8B illustrates an example of electric signals CD that flow through the heart 91 at subsequent times t11 to t20 and a current EV (t11 to t20) at that time. FIG. 8C illustrates an example of electric signals CD that flow through heart 91 at further subsequent times t21 to t30 and a current EV (t21 to t30) at that time.

The electrocardiographic current image generation portion 523 of the composite image generation portion 52 acquires, from the magnetic field intensity distribution image generation portion 522, a three-dimensional magnetic field intensity distribution model DM generated by the method illustrated in FIGS. 7A to 7C (dynamic three-dimensional magnetic field intensity distribution model DM that changes over time). In the heart 91, generally, a local current is generated (electric signals CD are generated) from the sinus node SN to an atrioventricular node AN in association with an over-time motion (heartbeat) of the heart 91 as illustrated in the left diagram of FIG. 8A, the current is transmitted (electric signals CD are generated) from the atrioventricular node AN to a His bundle HB as illustrated in the left diagram of FIG. 8B, and the current is transmitted (electric signals CD are generated) to a Purkinje's fiber PF as illustrated in the left diagram of FIG. 8C. As explained in FIG. 4, the three-dimensional magnetic field intensity distribution model DM is generated from information on the intensity and direction of the biomagnetic field MFh generated by the electric signals CD (biomagnetic field information). Thus, in the electrocardiographic current image generation portion 523, an over-time change in the electric signals CD at each position of the heart 91, i.e. an over-time change EX(t1-t30) in the current EV flowing through each position of the heart 91 can be determined in accordance with a well-known physical law such as Maxwell's equation using the three-dimensional magnetic field intensity distribution model DM (dynamic three-dimensional magnetic field intensity distribution model DM that changes over time) (in the right diagrams of FIGS. 8A to 8C). In FIGS. 8A to 8C, the figures were explained at times t1 to t30 for convenience, but, hereinafter, will be explained at times t1 to tn (n is a natural number).

As described above, the electrocardiographic current image generation portion 523 can acquire the over-time change EV(t1-tn) in the current EV flowing through each position of the heart 91 from the biomagnetic field information (indirectly via the three-dimensional magnetic field intensity distribution model DM). The electrocardiographic current image generation portion 523 may acquire the over-time change EV(t1-tn) in the current EV flowing through each position of the heart 91 by another method. For example, the electrocardiographic current image generation portion 523 may acquire the over-time change EV(t1-tn) in the current EV flowing through each position of the heart 91 directly from a detected value of the magnetic sensor array 10.

Figure 9:
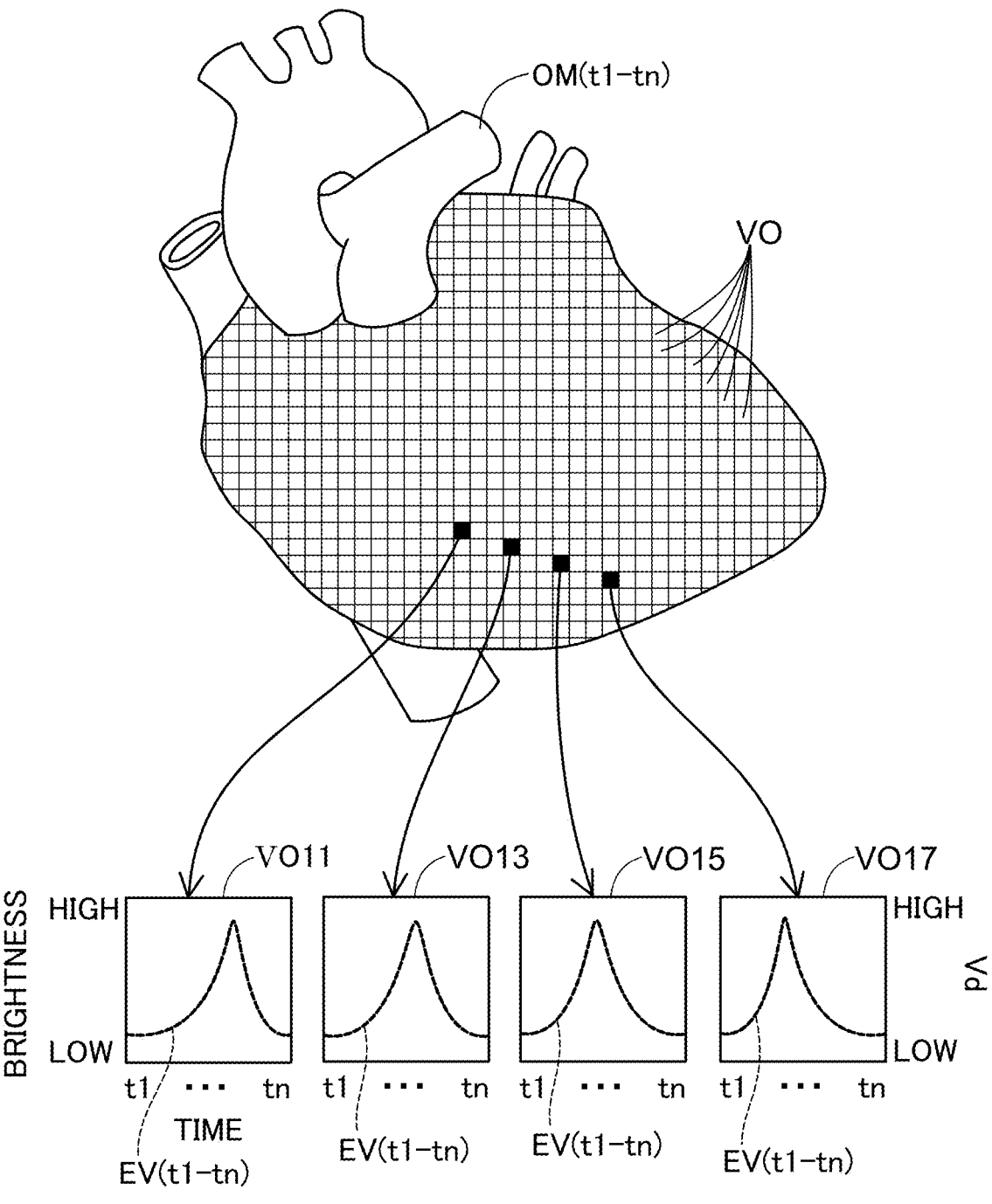
FIG. 9 is a schematic diagram illustrating a method for generating an electrocardiographic current image.

FIG. 9 is a schematic diagram illustrating a method for generating the electrocardiographic current image VI (t1 to tn). Subsequently, the electrocardiographic current image generation portion 523 generates an electrocardiographic current image VI (t1 to tn) in which the over-time change EV(t1-tn) in the current EV flowing through each position of the heart 91 is expressed by change in the color attribute. Specifically, the electrocardiographic current image generation portion 523 acquires, from the model image generation portion 521, the three-dimensional organ model OM (stereoscopic image data presenting external and internal shapes of the heart 91) generated by the method in FIGS. 3A and 3B. Herein, the three-dimensional organ model OM acquired by the electrocardiographic current image generation portion 523 means a dynamic three-dimensional organ model OM that changes over time, and is hereinafter also referred to as "three-dimensional organ model OM (t1 to tn)" for convenience.

Subsequently, in the electrocardiographic current image generation portion 523, the three-dimensional organ model OM (t1 to tn) is divided into voxels VO representing predetermined unit volume elements. Then, in the electro-cardiographic current image generation portion 523, the three-dimensional organ model OM (t1 to tn) is aligned with the over-time change EV(t1-tn) in the current EV flowing through each position of the heart 91, as determined by the method in FIGS. 8A to 8C. The alignment can be achieved e.g. by matching the current EV (t21 to t30) flowing to the Purkinje's fiber PF illustrated in the left diagram of FIG. 8C with the contour shape of the three-dimensional organ model OM (t1 to tn). This alignment allows the electrocardio-graphic current image generation portion 523 to acquire the over-time change EV(t1-tn) in the current EV flowing through each voxel VO, i.e. the over-time change EV(t1-tn) in the current EV flowing through each position of the heart 91. In the lower part of FIG. 9, the over-time changes EV(t1-tn) in the currents EV each flowing through voxels VO11, VO13, VO15, or VO17 at different positions are illustrated. As indicated by the dashed lines in the lower part of FIG. 9, the currents EV have different over-time changes EV(t1-tn) depending on the position of the voxel VO.

The electrocardiographic current image generation por-tion 523 generates an electrocardiographic current image VI (t1 to tn), in which each voxel VO is configured such that the hue and chroma are set to arbitrary values, and the brightness is set to a value according to the over-time change EV(t1-tn) in the current EV flowing through the correspond-ing voxel VO. In the example illustrated in the lower part of FIG. 9, the electrocardiographic current image generation portion 523 generates an electrocardiographic current image VI (t1 to tn) in which a brightness of a voxel VO is increased in proportion to a value of a current EV flowing through the voxel BVO. In this way, the electrocardiographic current image generation portion 523 can generate an electrocar-diographic current image VI (t1 to tn) in which voxels VO with a relatively high brightness (i.e., parts with a relatively high brightness) seem to move over time accompanying the over-time change EV(t1-tn) in the current EV. In other words, the electrocardiographic current image generation portion 523 according to the first embodiment generates an electrocardiographic current image VI (t1 to tn) in which a brightness of a voxel VO corresponding to a part through which a relatively high current EV flows among the respec-tive positions of the heart 91 at a predetermined time (e.g. time t10) is made higher than those of the other parts at the same time (e.g. time t10).

Figure 10:
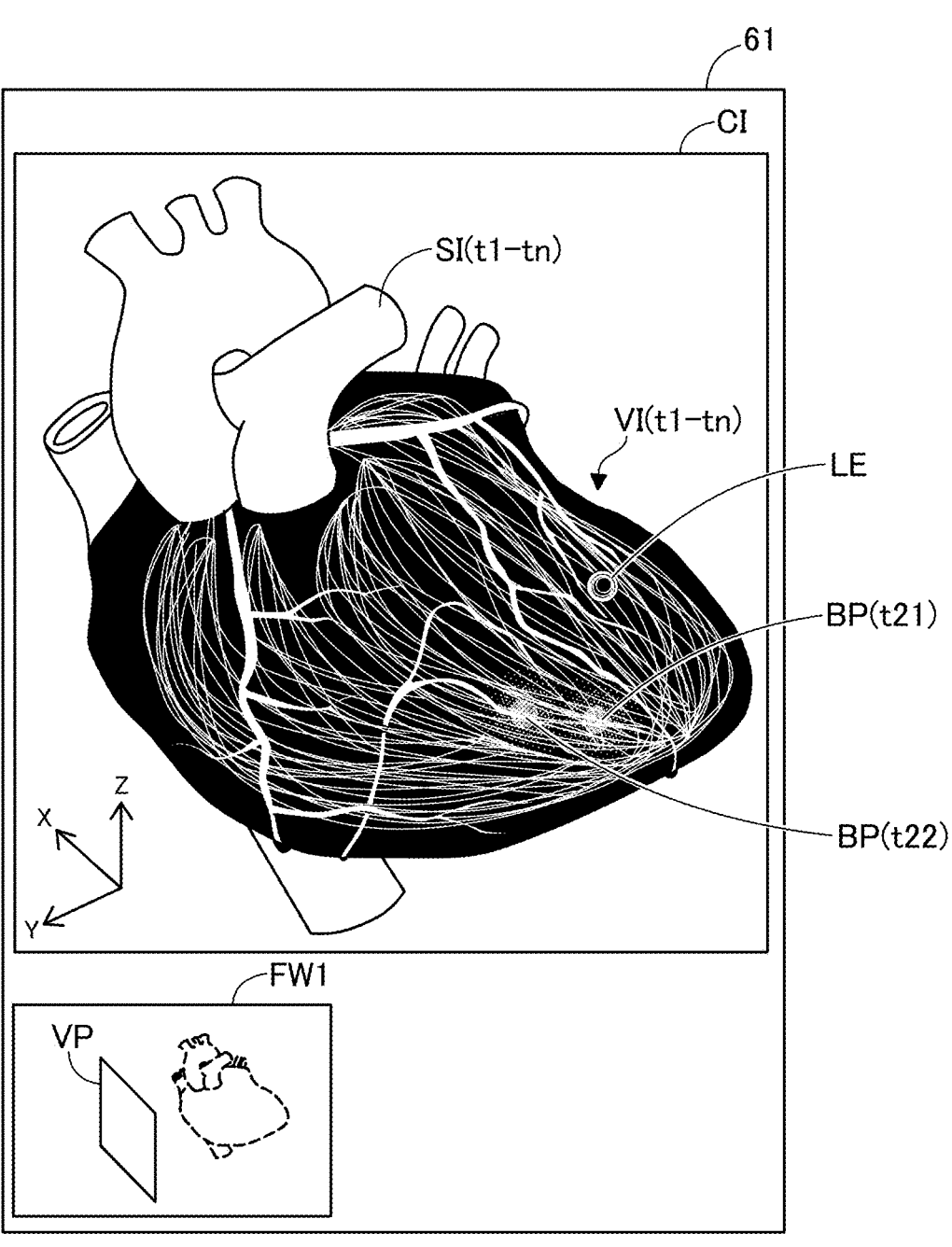
FIG. 10 is a diagram illustrating an example of a composite image.

FIG. 10 is a diagram illustrating an example of a com-posite image CI. The composite image generation portion 52 generates the composite image CI in which, on an organ model image SI (t1 to tn) generated by capturing a three-dimensional organ model OM (t1 to tn) on the virtual plane VP, an electrocardiographic current image VI (t1 to tn) on the same virtual plane VP is superposed. In the composite image generation portion 52, the generated composite image CI and a first window FW1 are displayed on a display screen 61 of the monitor 60. The first window FW1 displays an image presenting the heart 91 and an image presenting a positional relationship between the heart 91 and the virtual plane VP. The surgeon can change the position of the virtual plane VP in the composite image CI by operating the virtual plane VP displayed on the first window FW1 to change a positional relationship between the virtual plane VP and the image presenting the heart 91. In other words, the first window FW1 may serve as a graphical user interface for the user to control a positional relationship between the virtual plane VP and the image presenting the heart 91. In the example illustrated in FIG. 10, the virtual plane VP does not intersect with the image presenting the heart 91 in the first window FW1. For this reason, in the composite image CI, the organ model image SI (t1 to tn) presenting the appear-ance (outer surface) of the heart 91, and the electrocardio-graphic current image VI (t1 to tn) presenting the over-time change EV(t1-tn) in the current EV flowing through the same outer surface of the heart 91 are superposed.

In FIG. 10, the electrocardiographic current image VI (t1 to tn) in the composite images CI is illustrated in white. In this electrocardiographic current image VI (t1 to tn), a relatively bright part BP transitions over time according to the over-time change EV(t1-tn) in the current EV flowing through each position of the heart 91. For example, a relatively bright part BP (t21) at a certain time t21 and a relatively bright part BP (t22) at the next time t22 are at different position. By referring such a composite image CI, the surgeon can intuitively recognize the over-time change EV(t1-tn) in the current EV flowing through each position of the heart 91. At a site LE with an abnormal change in the current EV in the heart 91 (e.g., arrhythmia site in the heart 91), the brightness changes in a manner different from those of other normal sites (in the example illustrated in the figure, the brightness changes in a spiral shape). Thereby, the surgeon can also intuitively recognize the location of the lesion LE with abnormal change in the current EV.

In the electrocardiographic current image generation por-tion 523 and the composite image generation portion 52, the two-dimensional organ model OM can be processed in the same manner as explained in FIGS. 8 to 10 after dividing the model OM into pixels presenting predetermined unit area elements, also in the two-dimensional processing using the two-dimensional organ model OM and the two-dimensional magnetic field intensity distribution model DM.

Figure 11:
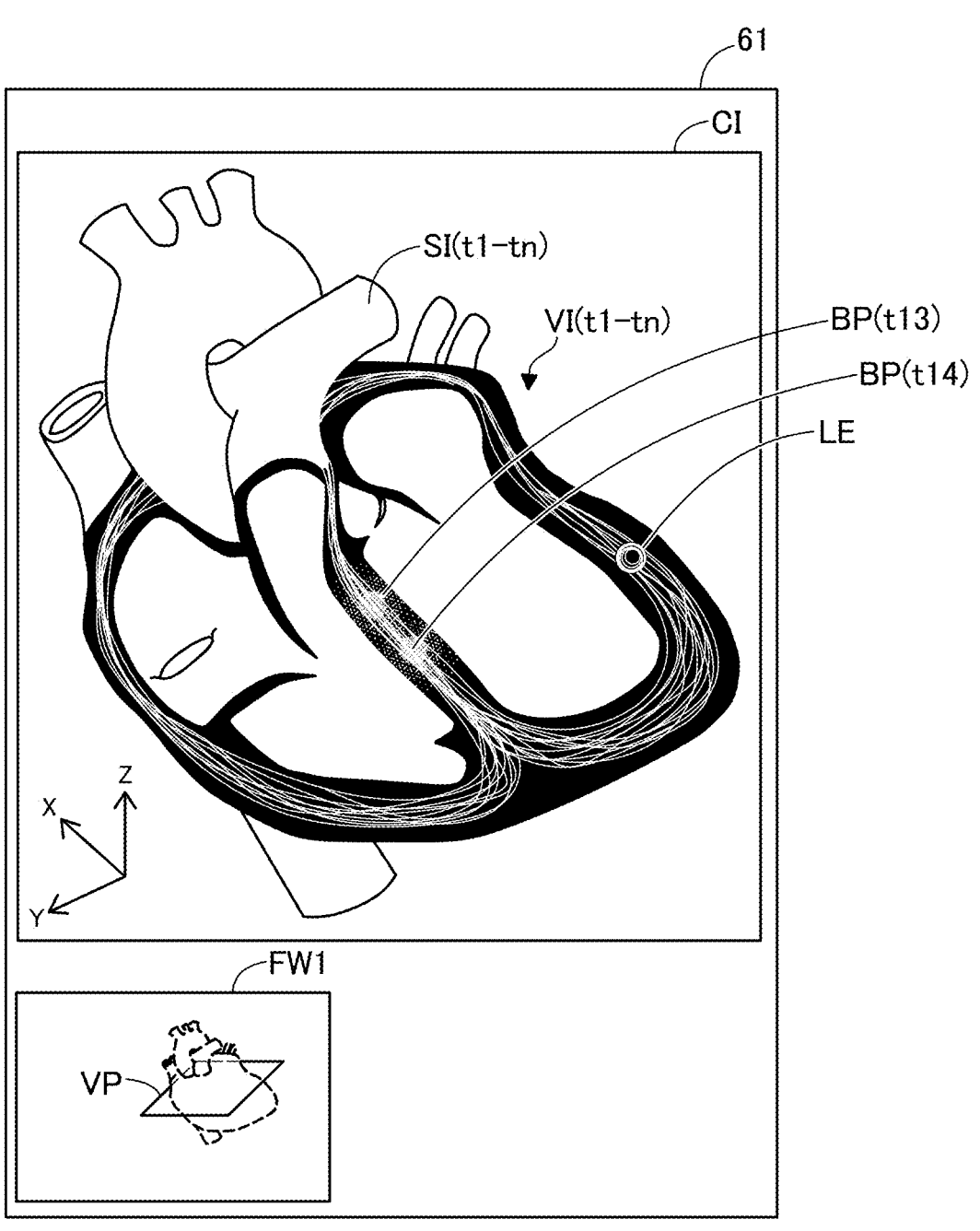
FIG. 11 is a diagram illustrating another example of the composite image.

FIG. 11 is a diagram illustrating another example of the composite image CI. In the example illustrated in FIG. 11, the virtual plane VP intersects with the image presenting the heart 91 in the first window FW1. For this reason, in the composite image CI, the organ model image SI (t1 to tn) presenting the cross-section of the heart 91 on the virtual plane VP, and the electrocardiographic current image VI (t1 to tn) presenting the over-time change EV(t1-tn) in the current EV flowing through the same cross-section of the heart 91 are superposed. Also in the composite image CI of FIG. 11, similarly to FIG. 10, in the electrocardiographic current image VI (t1 to tn), a relatively bright part BP transitions over time according to the over-time change EV(t1-tn) in the current EV flowing through each position of the heart 91. For example, a relatively bright part BP (t13) at a certain time t13 and a relatively bright part BP (t14) at the next time t14 are at different position.

Figure 12A:
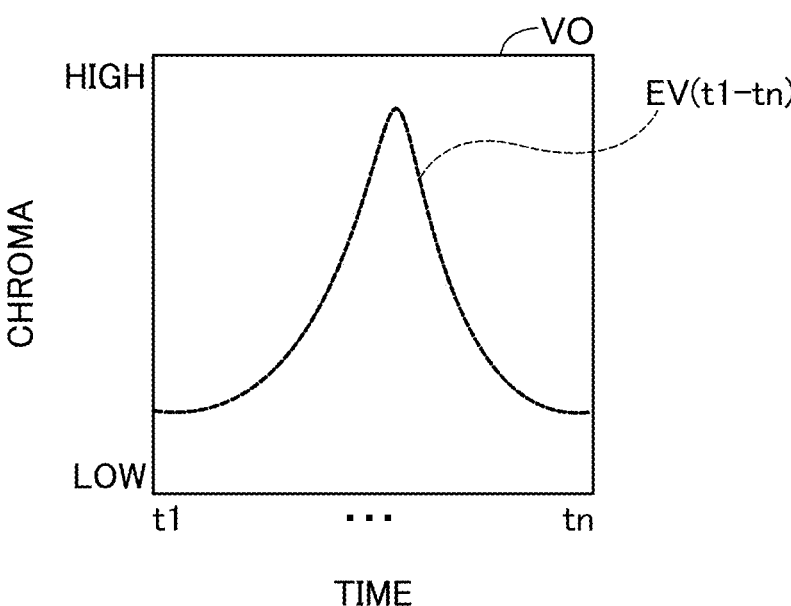
FIGS. 12A and 12B are diagrams illustrating an example of a change in a color attribute.
Figure 12B:
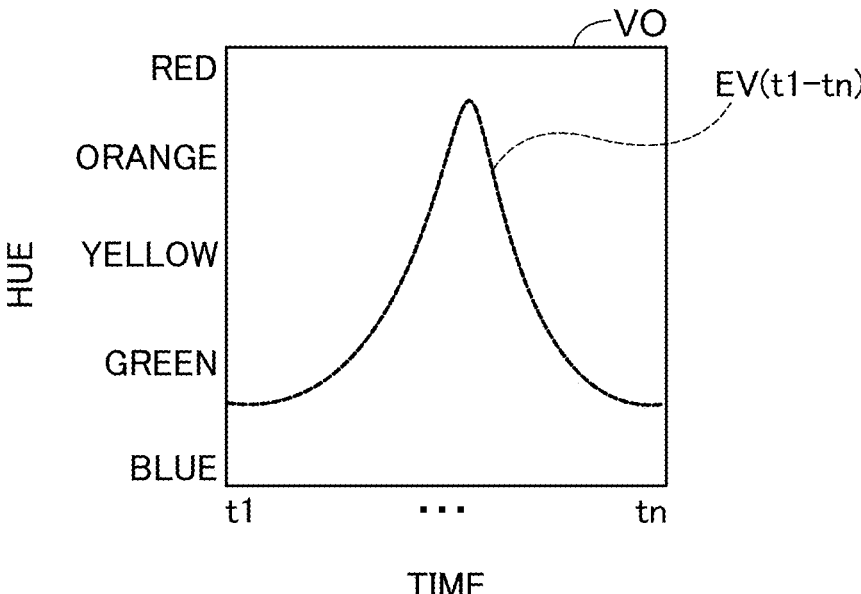

FIGS. 12A and 12B are diagrams illustrating an example of a change in a color attribute. FIG. 12A illustrates an example of changing a chroma, and FIG. 12B illustrates an example of changing a hue. As illustrated in FIG. 12A, when the electrocardiographic current image generation portion 523 generates the electrocardiographic current image VI (t1 to tn), each voxel VO may be configured such that the hue and brightness are set to arbitrary values, and the chroma is set to a value according to the over-time change EV(t1-tn) in the current EV flowing through the corresponding voxel VO. Also in such a way, the same effect as in the examples illustrated in FIGS. 9 to 11 with the changed brightness can be obtained. As illustrated in FIG. 12B, when the electrocardiographic current image generation portion 523 generates the electrocardiographic current image VI (t1 to tn), each voxel VO may be configured such that the brightness and chroma are set to arbitrary values, and the hue is set to a red-green-blue (RGB) color value according to the over-time change EV(t1-tn) in the current EV flowing through the corresponding voxel VO. Also in such a way, the same effect as in the examples illustrated in FIGS. 9 to 11 with the changed brightness can be obtained.

FIG. 9 illustrates an example of changing the brightness, FIG. 12A illustrates an example of changing the chroma, and FIG. 12B illustrates an example of changing the hue. However, the electrocardiographic current image generation portion 523 may generate an electrocardiographic current image VI (t1 to tn) in which any of the hue, chroma, brightness, and a combination thereof is changed.

Figure 13:
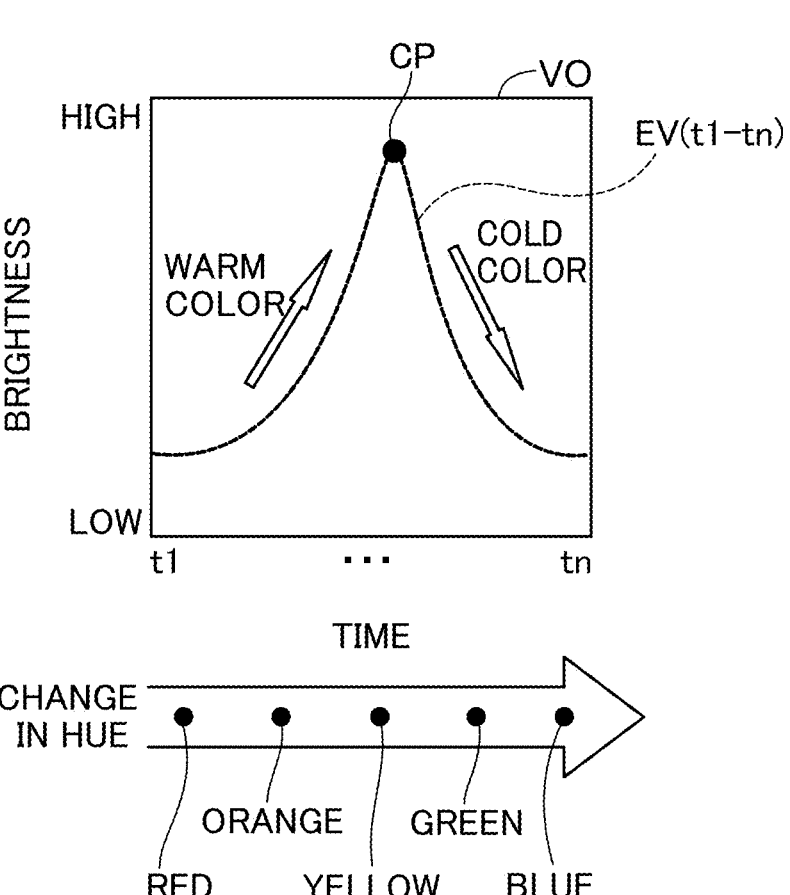
FIG. 13 is a diagram illustrating another example of the change in the color attribute.

FIG. 13 is a diagram illustrating another example of the change in the color attribute. FIG. 13 illustrates an example of changing a color attribute pattern. As illustrated in FIG. 13, when the electrocardiographic current image generation portion 523 generates the electrocardiographic current image VI (t1 to tn), a certain voxel VO is configured such that the color attribute is changed in a first pattern while the current EV rises over time (FIG. 13: while the current EV rises from time t1 to a crowning point CP). In the example illustrated in FIG. 13, in the first pattern, the hue is changed from red to yellow within a range of warm colors and the brightness is increased as the current EV rises. When the electrocardiographic current image generation portion 523 generates the electrocardiographic current image VI (t1 to tn), the aforementioned voxel VO is configured such that the color attribute is changed in a second pattern different from the first pattern while the current EV drops over time (FIG. 13: from after the current EV reaches the crowning point CP to time tn). In the example illustrated in FIG. 13, in the second pattern, the color attribute is changed from yellow to blue within a range of cold colors and the brightness is decreased as the current EV drops. In the electrocardiographic current image generation portion 523, each voxel VO of the three-dimensional organ model OM (t1 to tn) is processed in the same manner as described above to generate the electrocardiographic current image VI (t1 to tn).

According to the example illustrated in FIG. 13, the electrocardiographic current image generation portion 523 generates an electrocardiographic current image VI (t1 to tn) in which the color attribute is changed in the first pattern while the current value EV rises over time and changed in the second pattern while the current value EV drops over time at a certain position of the organ (a certain voxel VO of the heart 91). Thereby, the pattern of change in the color attribute allows the surgeon to intuitively recognize whether the current value EV at a certain position of an organ (a certain voxel VO of the heart 91) is rising or dropping.

As described above, the medical apparatus 1 according to the first embodiment makes it possible to generate a composite image CI in which the organ model image SI (t1 to tn) three-dimensionally or two-dimensionally presenting the heart 91 (organ), and the electrocardiographic current image VI (t1 to tn) presenting the over-time change EV(t1-tn) in the current EV flowing through each position of the heart 91 are superposed. Thereby, the surgeon can intuitively recognize the changes in the current EV flowing through each position of the heart 91 using the composite image CI. In the electrocardiographic current image VI (t1 to tn) in the composite image CI, the over-time change EV(t1-tn) in the current EV flowing through each position of the heart 91 is expressed by the change in the color attribute. Thus, compared to the conventional arrow indication for current vectors, the medical apparatus according to the disclosed embodiments has no concern that arrows indicating current vectors obstruct a surgeon's view and hinder the surgeon from checking a condition of the heart 91. As a result, a time required for detecting a lesion (e.g. arrhythmia site) can be shortened, and efficiency and safety of a procedure can be improved.

In the medical apparatus 1 according to the first embodiment, the electrocardiographic current image generation portion 523 generates the electrocardiographic current image VI (t1 to tn) in which the change in the color attribute is expressed by changing any of hue, chroma, brightness, and a combination thereof. Thereby, the surgeon can more intuitively recognize the change in the current EV flowing through each position of the heart 91 (organ). The electrocardiographic current image generation portion 523 generates an electrocardiographic current image VI (t1 to tn) in which at least one of hue, chroma, and brightness on a part (voxel VO) corresponding to a part through which a relatively high current EV flows is made higher than those on the other parts (voxels VO). Thereby, the surgeon can more intuitively recognize the change in the current EV flowing through each position of the heart 91.

Second Embodiment

Figure 14:
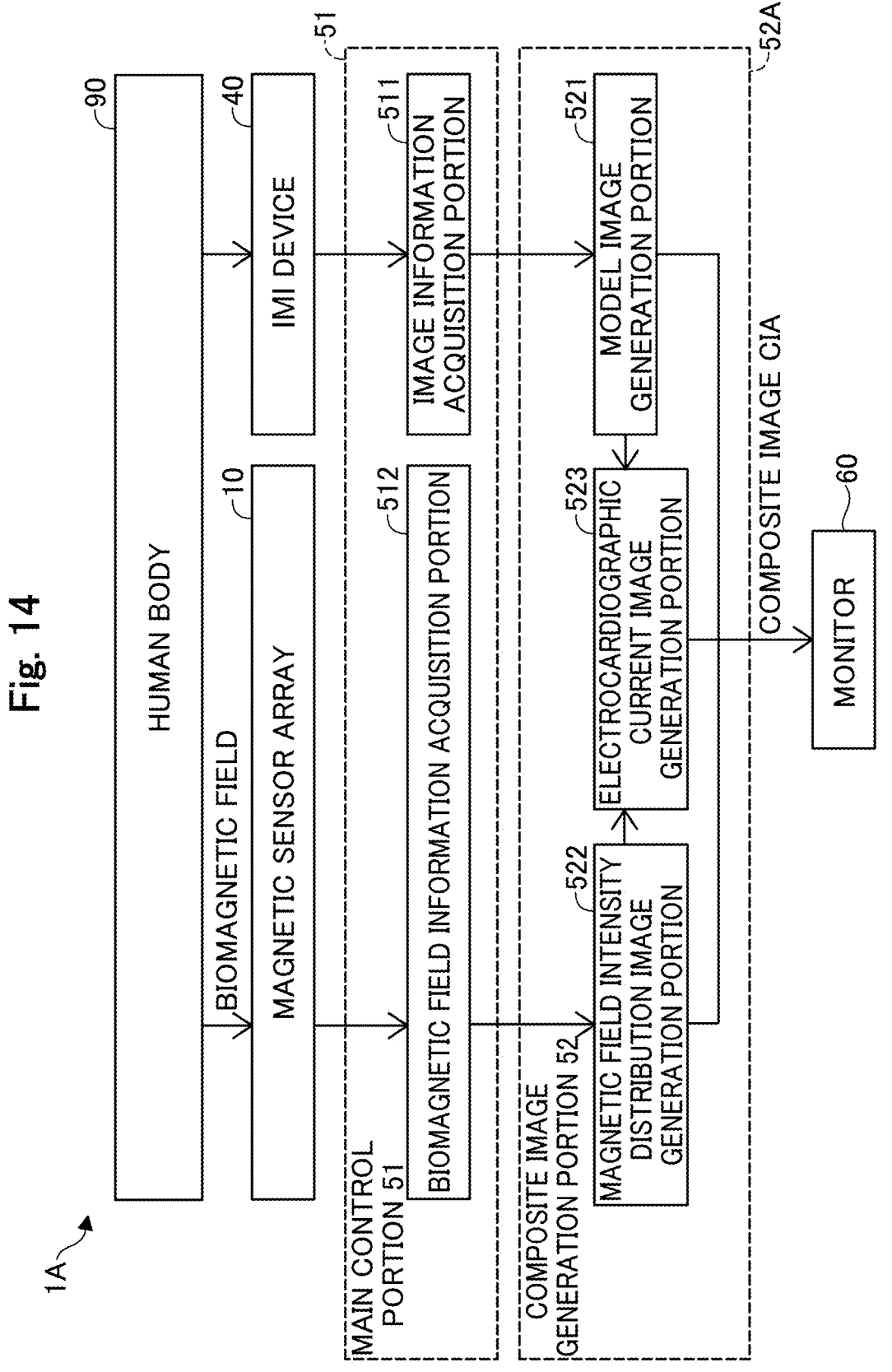
FIG. 14 is a functional block diagram illustrating a main control portion and a composite image generation portion according to the second embodiment.

FIG. 14 is a functional block diagram illustrating a main control portion 51 and a composite image generation portion 52A according to the second embodiment. A medical apparatus 1A according to the second embodiment includes the composite image generation portion 52A in place of the composite image generation portion 52 described in the first embodiment. The composite image generation portion 52A generates a composite image CIA in which, on the organ model image SI (t1 to tn) and the electrocardiographic current image VI (t1 to tn) described in the first embodiment, the magnetic field intensity distribution image MI (t1 to tn) on the same virtual plane VP is further superposed. The magnetic field intensity distribution image MI (t1 to tn) can be generated by capturing the three-dimensional magnetic field intensity distribution model DM generated by the method explained in FIGS. 7A to 7C on the virtual plane VP. In the composite image generation portion 52A, the generated composite image CIA, the first window FW1, and a second window FW2 are displayed on the display screen 61 of the monitor 60.

Figure 15:
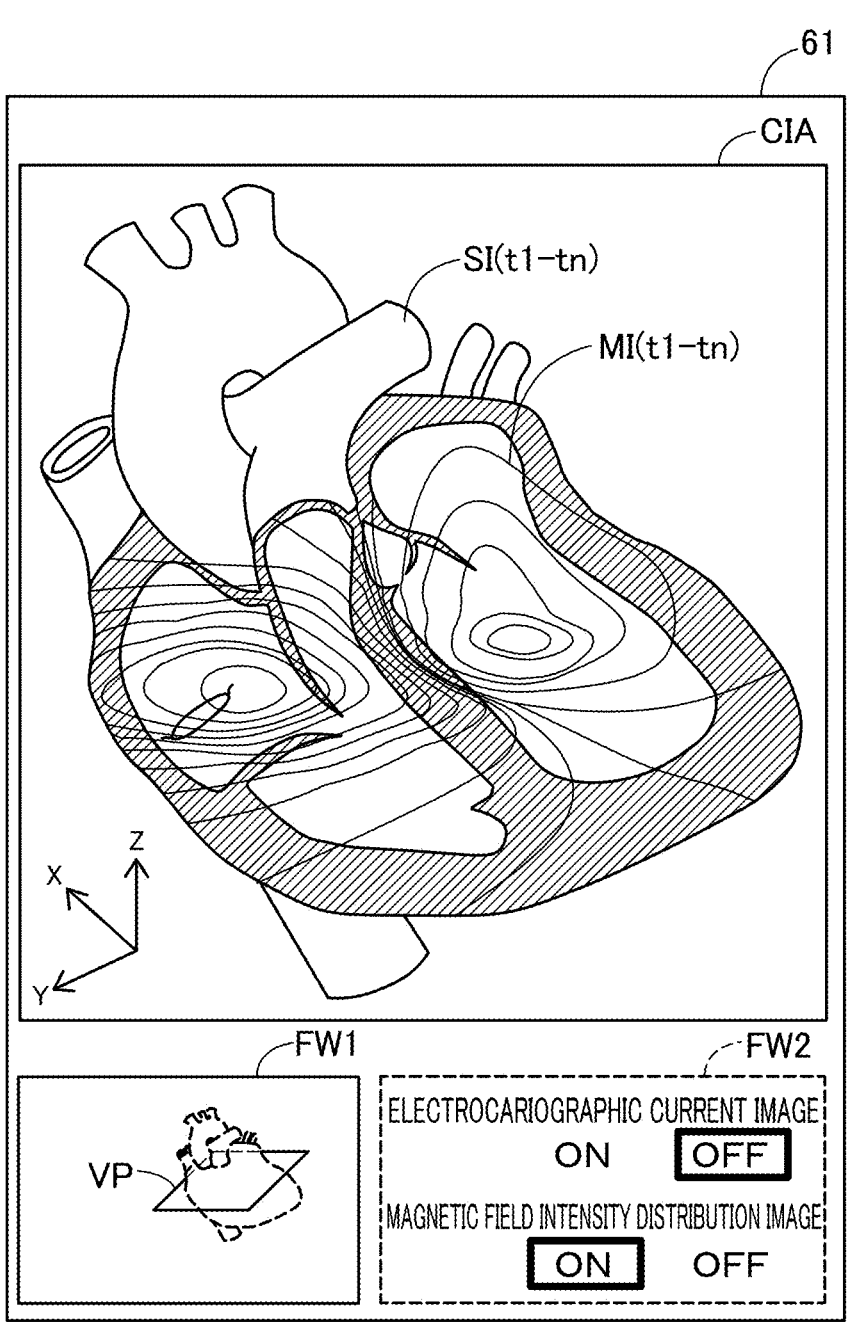
FIG. 15 is a diagram illustrating an example of the composite image according to the second embodiment.

FIG. 15 is a diagram illustrating an example of the composite image CIA according to the second embodiment. The first window FW1 is as described in the first embodiment. The second window FW2 displays an image indicating whether the electrocardiographic current image VI is displayed or not (ON/OFF), and whether the magnetic field intensity distribution image MI is displayed or not (ON/OFF). The surgeon can switch a type of an image superposed on the organ model image SI (t1 to tn) in the composite image CIA by selectively switching the ON/OFF displayed on the second window FW2. In other words, the second window FW2 may serve as a graphical user interface allowing a user to control what is displayed in the composite image CIA. In the example illustrated in FIG. 15, on the second window FW2, the display of the electrocardiographic current image VI is set to OFF (not displayed), and the display of the magnetic field intensity distribution image MI is set to ON (displayed). Thus, the upper part of the second window FW2 displays a composite image CIA in which the magnetic field intensity distribution image MI (t1 to tn) is superposed on the organ model image SI (t1 to tn).

Figure 16:
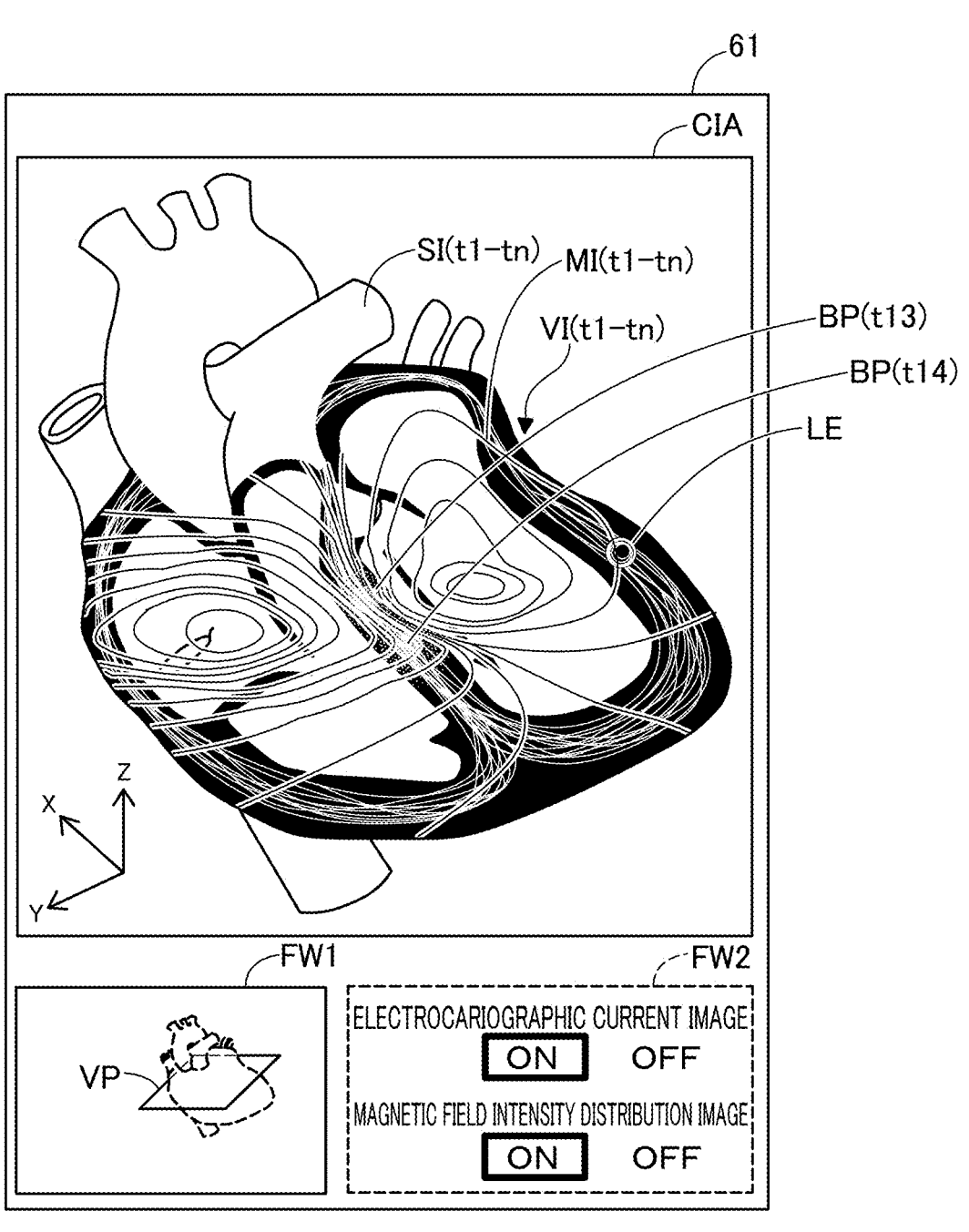
FIG. 16 is a diagram illustrating another example of the composite image according to the second embodiment.

FIG. 16 is a diagram illustrating another example of the composite image CIA according to the second embodiment. In the example illustrated in FIG. 16, on the second window FW2, the display of the electrocardiographic current image VI is set to ON (displayed), and the display of the magnetic field intensity distribution image MI is set to ON (displayed). Thus, the upper part of the second window FW2 displays a composite image CIA in which both the electro-cardiographic current image VI (t1 to tn) and the magnetic field intensity distribution image MI (t1 to tn) are super-posed on the organ model image SI (t1 to tn).

As described above, the medical apparatus 1A can be modified in various ways, and the composite image genera-tion portion 52A may generate and display the composite image CIA including another image different from the organ model image SI (t1 to tn) and the electrocardiographic current image VI (t1 to tn). In the aforementioned examples, although the magnetic field intensity distribution image MI (t1 to tn) was superposed on the composite image CIA, but other images may be superposed on the composite image CIA. As the other images, various images can be adopted, such as an image presenting a position of a lesion, and an image presenting a position of a medical device (catheter, etc.) inserted into the heart 91. In the composite image generation portion 52A, the second window FW2 for speci-fying a type of the image displayed as the composite image CIA may be further displayed in addition to the first window FW1 for specifying the virtual plane VP. Use of the second window FW2 can further improve usability of the medical apparatus 1A for the surgeon.

Also this medical apparatus 1A according to the second embodiment can exhibit a similar effect to the first embodi-ment described above. In the medical apparatus 1A accord-ing to the second embodiment, the composite image gen-eration portion 52A generates the composite image CIA in which the magnetic field intensity distribution image MI (t1 to tn) is further superposed on the organ model image SI (t1 to tn) and the electrocardiographic current image VI (t1 to tn). Thereby, the surgeon can recognize the intensity of the biomagnetic field MFh at each position of the heart 91 (organ) from the magnetic field intensity distribution image MI (t1 to tn) in the composite image CIA, and efficiency and safety of the procedure can be further improved.

Modifications of Present Embodiment

In the embodiments described above, a part of a configu-ration to be achieved by a hardware may be replaced with a software, or conversely, a part of a configuration to be achieved by a software may be replaced with a hardware. Furthermore, the disclosed embodiments are not limited to the embodiments described above and may be carried out in various aspects without departing from the spirit thereof, and for example, the following modifications are also pos-sible.

Modification 1

In the first and second embodiments, the configurations of the medical apparatuses 1 and 1A have been illustrated. However, the configuration of the medical apparatus 1 can be variously modified. For example, in the medical appara-tus 1, at least a part of the magnetic sensor array 10, the internal medical imaging device 40, the computer 50, the display portion 60, and the operating portion 70 may be configured as an integrated device. For example, the medical apparatus 1 may include other devices such as an MRI device, an electrocardiograph, an X-ray imaging device, and an ultrasonic probe. When the medical apparatus 1 includes an electrocardiograph, in the medical apparatus 1, a current value determined by the electrocardiographic current image generation portion 523 may be, e.g., confirmed, re-mea-sured, or corrected by comparing an actual value measured by the electrocardiograph with the over-time change EV(t1-tn) in the current EV determined by the electrocardiographic current image generation portion 523.

For example, in the electrocardiographic current image generation portion 523, the over-time change EV(t1-tn) in the current EV flowing through each position of the heart 91 may be determined by the following method a1 or method a2 different from the aforementioned method. In the meth-ods a1 and a2, the position of the medical device (catheter, etc.) in the heart 91 can be identified e.g. as follows.

A magnetic field generation portion composed of an electromagnet is installed in the medical device. The main control portion 51 of the medical apparatus 1 acquires second magnetic field information output from the magnetic sensor array 10 while the magnetic field generation portion (electromagnet) is energized. The second magnetic field information are magnetic field information with a combination of a biomagnetic field MFh and a device magnetic field generated by the magnetic field generation portion of the medical device (hereinafter also referred to as "biomagnetic/device magnetic mixed field"). The second magnetic field information include position information on the medi-cal device. Thereby, the main control portion 51 can identify a position of the magnetic field generation portion of the medical device by comparing the bio-magnetic field information described in the first embodiment with the second magnetic field informa-tion.

A magnetic field generation portion composed of a per-manent magnet is installed in the medical device. The main control portion 51 of the medical apparatus 1 can identify a position of the magnetic field generation portion of the medical device from an X-ray image acquired by an X-ray imaging device. This is because, when the magnetic field generation portion (magnetic force source) installed in the medical device is com-posed of a permanent magnet, a magnetic force inten-sity measurement value does not change by factors (mainly, time) other than a relative distance between the magnetic field generation portion on the X-ray image and the magnetic sensor array 10, and therefore the magnetic field generation portion can be identified as a magnetic force source that moves in conjunction with the operation of the medical device (i.e. movement of the medical device) rather than the heartbeat of the heart 91.

(a1) An electrode may be installed in the medical device to determine the over-time change EV(t1-tn) in the current EV flowing through each position of the heart 91 by a potential measurement using a medical device inserted into the inside of the heart 91. In this case, the potential change is measured at a specific point inside the heart 91 for an arbitrary time T, and then the measurement point is moved to acquire required data of the over-time change in the potential in the heart region. The time T can be set to a value corresponding to a previously acquired heartbeat cycle of the heart 91, and may be m times (m is a natural number) the heartbeat cycle of the heart 91. In the electrocardiographic current image generation portion 523, the potential change thus acquired is replaced by the over-time change EV(t1-tn) in the current EV. In principle, only unit conversions can be used for the replacement. In the electrocardiographic current image generation portion 523, signal correction such as noise reduction may be carried out along with the replacement. If the medical device to be inserted into the heart 91 is a catheter having a basket structure, the potential and current can be replaced by each other while carrying out the measurement in real time.

(a2) A magnetic sensor may be installed in the medical device to determine the over-time change EV(t1-tn) in the current EV flowing through each position of the heart 91 by a magnetism measurement using the medical device inserted into the inside the heart 91. In this case, the change in the magnetism is measured at a specific point inside the heart 91 for an arbitrary time T, and then the measurement point is moved to acquire required data of the over-time change in the magnetism in the heart region. Explanation of the time T is the same as in the method a1. In the electrocardiographic current image generation portion 523, the change in the magnetism thus acquired is converted into the over-time change EV(t1-tn) in the current EV in accordance with a well-known physical law such as Maxwell's equation. If the medical device to be inserted into the heart 91 is a catheter having a basket structure, the magnetism and the current can be converted into each other while carrying out the measurement in real time.

As is well known, the over-time changes in the magnetism, potential, and current correlate with each other. Consequently, in the method described in the first embodiment and in methods a1 and a2 above, the electrocardiographic current image generation portion 523 may determine the over-time change EV(t1-tn) using impedance data of a myocardium of the heart 91 together with Maxwell's equation.

Modification 2

In the first and second embodiments above, examples of the image generated by the composite image generation portion 52 or 52A and displayed on the display screen 61 were described. However, the image displayed on the display screen 61 can be modified in various ways. For example, at least one of the first window FW1 and the second window FW2 may be omitted. For example, a third window may be displayed on the display screen 61 to allow selection of the method of changing the color attribute on the electrocardiographic current image VI (t1 to tn) (method explained in FIG. 9, FIGS. 12A and 12B, and FIG. 13). For example, the display screen 61 may display various images such as an MRI image, an image presenting electrocardiographic measurement data, an image presenting pulse or the like, and an image for explaining a procedure. For example, on the composite image CI, an image presenting a position of the medical device or a position of a lesion may be further superposed. For example, on the composite image CI, an image presenting a specific site (sinus node, atrioventricular node, His bundle, Purkinje's fiber, etc.) of the heart 91 may be further superposed.

Modification 3

Each of the configurations of the medical apparatus 1 and 1A according to the first and second embodiments described above and the configurations of Modifications 1 and 2 described above may be appropriately combined. For example, in the configuration described in the second embodiment, a variation of the change in the color attribute in the electrocardiographic current image VI (t1 to tn) explained in FIG. 9, FIGS. 12A and 12B, and FIG. 13 may be adopted.

The present aspect has been described above based on the embodiments and the modifications; however, the embodiments according to the above aspects are provided to facilitate understanding of the present aspect and not to limit the aspect. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. The present aspect may be modified and improved without departing from the spirit thereof and the scope of claims, and the present aspect includes equivalents thereof. Furthermore, the technical features may be omitted as appropriate unless they are described as essential in this description.

DESCRIPTION OF REFERENCE NUMERALS

1, 1A Medical apparatus
10 Magnetic sensor array
11 Magnetic sensor
40 Internal medical imaging device
50 Computer
51 Main control portion
52, 52A Composite image generation portion
60 Monitor
61 Display screen
70 Operating portion
90 Human body
91 Heart
95 Bed
511 Image information acquisition portion
512 Biomagnetic field information acquisition portion
521 Model image generation portion
522 Magnetic field intensity distribution image generation portion
523 Electrocardiographic current image generation portion
VP Virtual plane
OM Three-dimensional organ model
DM Three-dimensional magnetic field intensity distribution model
SI Organ model image
VI Electrocardiographic current image
MI Magnetic field intensity distribution image
CI, CIA Composite image
FW1 First window
FW2 Second window
HB His bundle
LE Lesion
PF Purkinje's fiber
SN Sinus node

What is claimed is:
1. A medical apparatus comprising:
circuitry configured to:
acquire image information regarding an image of an organ in a living body;
acquire biomagnetic field information from a biomagnetic field generated by the organ;

generate, from the image information, an organ model image of the organ two-dimensionally or three-dimensionally expressed;

generate an electrocardiogramrent image in which an over-time change in a current flowing through each position of the organ, acquired from the biomagnetic field information, is expressed by a change in a color attribute; and generate a composite image in which the organ model image and the electrocardiograma current image are superposed, wherein, at a certain position of the organ, when a current value rises from a predetermined value, the circuitry is configured to generate the electrocardiograment image with the color attribute changed in a first pattern, and when the current value drops from the predetermined value, the circuitry is configured to generate the electrocardiograment image with the color attribute changed in a second pattern different from the first pattern.

2. The medical apparatus according to claim 1, wherein the circuitry is configured to express the change in the color attribute by changing any of hue, chroma, brightness, and a combination thereof.

3. The medical apparatus according to claim 2, wherein the circuitry is configured to generate the electrocardiogramrent image in which at least one of hue, chroma, and brightness on a part through which a relatively high current flows among the positions of the organ at a predetermined time is made higher than those of other parts at a same time.

4. The medical apparatus according to claim 1, wherein the biomagnetic field information includes information on a magnetic field intensity distribution of the biomagnetic field generated by the organ, and the circuitry is further configured to:

generate, from the biomagnetic field information, a magnetic field intensity distribution image presenting an intensity of the biomagnetic field at each position of the organ, and generate a composite image in which the magnetic field intensity distribution image is further superposed on the organ model image and the electrocardiogra current image.

5. The medical apparatus according to claim 1, wherein the circuitry is further configured to generate a first graphical user interface to be displayed along with the composite image, the first graphical user interface configured to control including whether the magnetic field intensity distribution image and/or the electrocardiogramarrent image are superimposed on the organ model image.

6. The medical apparatus according to claim 5, wherein the circuitry is further configured to generate a second graphical user interface to be displayed along with the composite image, the second graphical user interface configured to display and control a position of a virtual plane on which the organ model image is generated.

7. The medical apparatus according to claim 1, wherein the circuitry is further configured to generate a graphical user interface to be displayed along with the composite image, the graphical user interface configured to allow a user to control what is to be displayed in the composite image including the organ model image.

8. The medical apparatus according to claim 7, wherein the graphical user interface is configured to allow the user to control a position of a virtual plane on which the organ model image is generated.

9. The medical apparatus according to claim 7, wherein the graphical user interface is configured to allow the user to control what is superposed on the organ model image.

10. The medical apparatus according to claim 1, wherein the circuitry is further configured to:

provide a first window and a second window, wherein the first window is configured to display an image presenting the organ and an image presenting a positional relationship between the organ and a virtual plane, the second window is configured to display the composite image, and dynamically update the composite image displayed in the second window to show a cross-section corresponding to a new position of the virtual plane in response to an operation of the virtual plane displayed on the first window.

11. An image generation method comprising:

acquiring image information of an image of an organ in a living body;

acquiring biomagnetic field information from a biomagnetic field generated by the organ;

generating, from the image information, an organ model image of the organ two-dimensionally or three-dimensionally expressed;

generating an electrocardiogramrent image in which an over-time change in a current flowing through each position of the organ, acquired from the biomagnetic field information, is expressed by a change in a color attribute; and generating a composite image in which the organ model image and the electrocardiograment image are superposed, wherein, at a certain position of the organ, when a current value rises from a predetermined value, generating the electrocardiogramt image with the color attribute changed in a first pattern, and when the current value drops from the predetermined value, generating the electrocardiograment image with the color attribute changed in a second pattern different from the first pattern.

12. The image generation method according to claim 11, wherein generating the electrocardiograment image expresses the change in the color attribute by changing any of hue, chroma, brightness, and a combination thereof.

13. The image generation method according to claim 11, further comprising generating a graphical user interface to be displayed along with the composite image, the graphical user interface configured to allow a user to control what is to be displayed in the composite image including the organ model image.

14. The image generation method according to claim 11, wherein the biomagnetic field information includes information on a magnetic field intensity distribution of the biomagnetic field generated by the organ, and the method further comprising:

generating, from the biomagnetic field information, a magnetic field intensity distribution image presenting an intensity of the biomagnetic field at each position of the organ, and generating a composite image in which the magnetic field intensity distribution image is further superposed on the organ model image and the electrocardiogra current image.

15. The image generation method according to claim 11, further comprising:

providing a first window and a second window, wherein the first window is configured to display an image presenting the organ and an image presenting a positional relationship between the organ and a virtual plane, the second window is configured to display the composite image, and dynamically updating the composite image displayed in the second window to show a cross-section corresponding to a new position of the virtual plane in response to an operation of the virtual plane displayed on the first window.

16. A non-transitory computer readable storage device having computer readable instructions that when executed by circuitry cause the circuitry to:

acquire image information of an image of an organ in a living body;

acquire biomagnetic field information from a biomagnetic field generated by the organ;

generate, from the image information, an organ model image of the organ two- dimensionally or three-dimensionally expressed;

generate an electrocardiogramrent image in which an over-time change in a current flowing through each position of the organ, acquired from the biomagnetic field information, is expressed by a change in a color attribute; and generate a composite image in which the organ model image and the electrocardiogra current image are superposed, wherein, at a certain position of the organ, when a current value rises from a predetermined value, the circuitry is caused to generate the electrocardiogramrent image with the color attribute changed in a first pattern, and when the current value drops from the predetermined value, the circuitry is caused to generate the electrocardiogramt image with the color attribute changed in a second pattern different from the first pattern.

17. The non-transitory computer readable storage device according to claim 16, wherein the biomagnetic field information includes information on a magnetic field intensity distribution of the biomagnetic field generated by the organ, and the circuitry is further caused to:

generate, from the biomagnetic field information, a magnetic field intensity distribution image presenting an intensity of the biomagnetic field at each position of the organ, and generate a composite image in which the magnetic field intensity distribution image is further superposed on the organ model image and the electrocardiogra current image.

18. The non-transitory computer readable storage device according to claim 16, wherein the circuitry is further caused to:

provide a first window and a second window, wherein the first window is configured to display an image presenting the organ and an image presenting a positional relationship between the organ and a virtual plane, the second window is configured to display the composite image, and dynamically update the composite image displayed in the second window to show a cross-section corresponding to a new position of the virtual plane in response to an operation of the virtual plane displayed on the first window.

* * * * *